United States Patent
Chou et al.

(10) Patent No.: US 10,429,628 B2
(45) Date of Patent: Oct. 1, 2019

(54) MULTIFOCAL METHOD AND APPARATUS FOR STABILIZATION OF OPTICAL SYSTEMS

(71) Applicant: THE UNIVERSITY OF BRITISH COLUMBIA, Vancouver (CA)

(72) Inventors: Keng C. Chou, Vancouver (CA); Reza Tafteh, Richmond (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 15/568,770

(22) PCT Filed: Apr. 22, 2016

(86) PCT No.: PCT/CA2016/050474
§ 371 (c)(1),
(2) Date: Oct. 23, 2017

(87) PCT Pub. No.: WO2016/168941
PCT Pub. Date: Oct. 27, 2016

(65) Prior Publication Data
US 2018/0149855 A1    May 31, 2018

Related U.S. Application Data

(60) Provisional application No. 62/151,569, filed on Apr. 23, 2015.

(51) Int. Cl.
*G02B 21/26*    (2006.01)
*G02B 27/32*    (2006.01)
(Continued)

(52) U.S. Cl.
CPC ......... *G02B 21/26* (2013.01); *G01N 21/6458* (2013.01); *G02B 21/16* (2013.01);
(Continued)

(58) Field of Classification Search
CPC ...... G02B 21/26; G02B 21/241; G02B 21/34; G02B 21/16; G02B 21/6458;
(Continued)

(56) References Cited

U.S. PATENT DOCUMENTS 7,928,409 B2 * 4/2011 Perkins ............... G01Q 10/065
250/491.1
8,564,792 B2 * 10/2013 Zhuang ............ G01N 21/6428
356/624
(Continued)

FOREIGN PATENT DOCUMENTS

WO    2013063096 A1    5/2013

*Primary Examiner* — Yara B Green
(74) *Attorney, Agent, or Firm* — Oyen Wiggs Green & Mutala LLP

(57) ABSTRACT

Methods and apparatus for deep microscopic super resolution imaging use two independent and variable focal planes. Movements of fiducial markers imaged using one focal plane are monitored and used to provide real-time or near real-time correction for sample drift. A second focal plane may be used to collect light for super-resolution imaging of a sample. A prototype embodiment has produced low drift when imaging many microns deeper than the fiducial markers.

35 Claims, 11 Drawing Sheets

(51) Int. Cl.
  *G02B 27/00*   (2006.01)
  *G02B 21/24*   (2006.01)
  *G02B 21/36*   (2006.01)
  *G06T 7/70*    (2017.01)
  *G01N 21/64*   (2006.01)
  *G02B 21/16*   (2006.01)
  *G02B 21/34*   (2006.01)
  *G02B 3/14*    (2006.01)
  *G02B 21/06*   (2006.01)

(52) U.S. Cl.
  CPC ......... *G02B 21/241* (2013.01); *G02B 21/244* (2013.01); *G02B 21/34* (2013.01); *G02B 21/367* (2013.01); *G02B 27/0075* (2013.01); *G02B 27/32* (2013.01); *G06T 7/70* (2017.01); *G01N 2021/6463* (2013.01); *G01N 2201/063* (2013.01); *G02B 3/14* (2013.01); *G02B 21/06* (2013.01); *G02B 21/361* (2013.01); *G06T 2207/10056* (2013.01); *G06T 2207/10064* (2013.01); *G06T 2207/30204* (2013.01)

(58) Field of Classification Search
  CPC ........ G02B 21/361; G02B 21/06; G06T 7/70; G06T 2207/10064; G06T 2207/10056
  See application file for complete search history.

(56) References Cited

U.S. PATENT DOCUMENTS

| | | |
|---|---|---|
| 2005/0141081 A1 | 6/2005 | Olschewski |
| 2011/0002530 A1* | 1/2011 | Zhuang ............. G01N 21/6428 382/154 |
| 2012/0002031 A1* | 1/2012 | Pertsinidis ............ G02B 21/18 348/79 |
| 2012/0300293 A1 | 11/2012 | Selvin et al. |
| 2013/0027518 A1* | 1/2013 | MacKay ................ G02B 21/26 348/46 |
| 2013/0070339 A1 | 3/2013 | Pretorius |
| 2013/0120539 A1* | 5/2013 | Foelling ............ G02B 27/0075 348/49 |
| 2016/0085062 A1* | 3/2016 | Kalkbrenner ........ G02B 21/006 348/49 |

* cited by examiner

MULTIFOCAL METHOD AND APPARATUS FOR STABILIZATION OF OPTICAL SYSTEMS

CROSS-REFERENCE TO RELATED APPLICATION

This application claims convention priority from U.S. patent application No. 62/151,569 filed 23 Apr. 2015 which is hereby incorporated herein by reference for all purposes. For purposed of the United States of America, this application claims the benefit under 35 U.S.C. § 119 of application No. 62/151,569 filed 23 Apr. 2015, and entitled Three dimensional Stabilization System for Optical Imaging Using Independent Variable Focal Planes.

FIELD

This disclosure relates to microscopy. Various embodiments measure and compensate for sample drift. The invention has particular application to high-resolution and super-resolution microscopy.

BACKGROUND

Super-resolution microscopy techniques permit exceedingly high resolution imaging of specimens using optical radiation. The resolution can be finer than the wavelength of the optical radiation used for imaging. Such techniques include including stimulated emission depletion (STED) and RESOLFT microscopy (see e.g. Hell S W. Nat. Biotech. 2003; 21:1347; and Hell S W. Science. 2007; 316:1153.), saturated structured illumination microscopy (SSIM) (see e.g. Gustafsson M G L. Proc. Natl. Acad. Sci., USA. 2005; 102:13081), stochastic optical reconstruction microscopy (STORM) (see e.g. Rust M J, Bates M, Zhuang X. Nat. Meth. 2006; 3:793; Bates M, Huang B, Dempsey G T, Zhuang X. Science. 2007; 317:1749; and Huang, Bo "Three-dimensional Super-resolution Imaging by Stochastic Optical Reconstruction Microscopy" Science 319 (5864): 810-813 (2008)), photoactivated localization microscopy (PALM) (see e.g. Betzig E, et al. Science. 2006; 313:1642; and Hess S T, Girirajan T P K, Mason M D. Biophys. J. 2006; 91:4258) and other methods using similar principles (see e.g. Sharonov A, Hochstrasser R M. Proc. Natl. Acad. Sci., USA. 2006; 103:18911; Egner A, et al. Biophys. J. 2007; 93:3285; and Bock H, et al. Appl. Phys. B. 2007; 88:161). Such techniques can achieve lateral resolutions of better than 50 nm. Many of these techniques are single-molecule-localization (SML) techniques which create conditions in which light is emitted from single molecules. The knowledge that light emissions occur at discrete locations can be used to create exceptionally high resolution images.

STORM uses photo-switchable fluorescent probes to temporally separate the otherwise spatially overlapping images of individual molecules, allowing for precise localization of individual fluorescent labels in the sample. Although three dimensional (3D) STORM based on astigmatic single-molecule localizations has been gaining popularity, high accuracy deep imaging still faces many challenges. In STORM microscopy, an acquisition time of several minutes is often needed to accumulate a sufficient number of fluorophore positions and construct an informative image.

Sample drift is movement of a sample being imaged relative to imaging apparatus (e.g. relative to an objective lens and imaging sensor such as a camera). Sample drift compromises the precision and accuracy of imaging. Sample drift can occur in all three dimensions, and arises from a wide number of sources including mechanical vibrations and other mechanical movements, temperature changes, temperature gradients and the like.

Although the lateral accuracy of fluorophore localization by super-resolution imaging techniques such as STORM can be better than 10 nm, sample drift due to thermal gradients or mechanical motions can easily be in the hundreds of nanometers. In conventional fluorescence microscopy typical resolutions are on the order of 300 nm or more and sample drifts of 100 nm may be tolerable. In super-resolution microscopy a sample drift of 100 nm or more during acquisition may destroy the high resolution nature of the image. Therefore minimizing sample drift often becomes the most important factor in determining the performance of a super-resolution microscope.

Furthermore, the above techniques can require relatively long data acquisition times (e.g. times on the order of several minutes or more are not uncommon). Such long data acquisition place even higher demands on minimizing sample drift. SML methods may routinely take minutes to hours to obtain a single image. In SML-based super-resolution methods, minimizing sample drift over long periods of time is desirable.

Various approaches to correcting for positional drift have been described in the literature. These include online correction using fiducial markers (see e.g. Pertsinidis, A., Zhang, Y. & Chu, S. Nature 466, 647-651 (2010) and Carter, A. R. et al. Appl. Opt. 46, 421-427 (2007)) as well as offline processing algorithms using a bright-field image (see e.g. Mennella, V. et al. Nat. Cell Biol. 14, 1159-1168 (2012)) or consecutive blink tracking (see e.g. Geisler, C. et al. Opt. Express 20 (2012)). Other references describing image stabilization or drift correction techniques include:

- Ashley R. Carter et al: "Stabilization of an optical microscope to 0.1 nm in three dimensions", APPLIED OPTICS, vol. 46, no. 3, 1 Jan. 2007 (2007 Jan. 1), page 421
- WO2013063096A1 Multifunction autofocus system and method for automated microscopy;
- US20130070339 Method and device for image stabilization in an optical observation or measurement instrument;
- US20050141081 Method for correcting drift in an optical device; and
- U.S. Pat. No. 7,928,409 Real-time, active picometer-scale alignment, stabilization, and registration in one or more dimensions.

Offline processing algorithms have difficulty in correcting for large drifts. Real-time drift correction techniques using fiducial markers have so-far produced the best super-resolution images. Fiducial markers, typically fluorescent beads affixed to a coverslip, are used as reference points to measure and correct for drift. The positions of bright fiducial markers can typically be determined within an error of a few nm. However, when the objective lens is focused at a depth into the sample greater than the depth of field provided by the objective lens (typically on the order of 0.5 µm or less), the fiducial markers on the coverslip are out of focus making it difficult or impossible to obtain accurate measurements of drift.

There is a need for practical and cost-effective ways to compensate for sample drift in super-resolution microscopy.

SUMMARY

The invention has a number of aspects. These include, without limitation:

methods for super-resolution imaging which compensate for sample drift;

apparatus for compensating for sample drift in microscopy—such apparatus may be integrated into a microscope or may be provided as an add-on or retrofit system to an existing microscope.

Methods according to some embodiments acquire light from a sample using one focal plane (a sample focal plane) and acquire light from one or more fiducial markers using a different focal plane (a fiducial marker focal plane). The same objective lens may be used to acquire both the light from the sample and the light from the fiducial markers. For example, the fiducial marker focal plane may coincide with fiducial markers such as microbeads, nanoparticles, or quantum dots attached to a coverslip to yield images of the fiducial markers that permit precise determination of changes in position of the fiducial markers.

The sample focal plane may be deep within the sample (e.g. deeper than a depth of field of the objective lens). In some embodiments, the sample focal plane is more than 1 μm or more than 5 μm deeper than the fiducial marker focal plane. In some embodiments, the sample focal plane is spaced deeper than the fiducial marker focal plane by at least 2, 3, or 5 times a depth of field of the imaging system used to image target features in the image focal plane.

Real-time nanometer-scale drift correction may be performed based on the observed changes in position of the fiducial markers. This may provide essentially drift-free images that more faithfully represent a labeled structure of a sample being imaged than images for which drift correction is not performed.

Fiducial markers and a region of interest in a sample may be imaged using separate focal planes in various ways. These include:

Providing separate imaging systems which include separate imaging light detectors (e.g. cameras) for collecting light from the sample and the fiducial markers. One or both of the imaging systems include one or more variable focusing elements such that each of the sample focal plane and the fiducial marker focal plane may be set to a corresponding desired depth. The optical paths of both imaging systems pass through the same objective lens. Other parts of the optical paths of the imaging systems may also overlap.

Providing an optical system that focuses light from the sample to a first area of an imaging light detector and another optical system that focuses light from the fiducial markers onto a second area of the imaging light detector.

Providing one variable-focus imaging system and a controller configured to focus the imaging system on the sample focal plane to obtain light from the sample and periodically re-focus the imaging system on the fiducial marker focal plane to image the fiducial markers. The images of the fiducial markers may be obtained with relatively brief exposures obtained frequently enough to provide near real-time drift correction. This option has the advantage of reduced cost but may provide poorer performance than the options mentioned above which can provide continuous correction for sample drift.

In embodiments which provide separate optical paths for directing light from the sample and light from the fiducial markers, light from the sample and light from the fiducial markers may be separated using suitable filters. In some embodiments light from the sample and light from the fiducial markers have different wavelengths and wavelength-selective filters such as dichroic mirrors may be used to separate light from these two sources. Focusing elements may be provided in parts of one or both optical paths that are not common to facilitate establishment of the sample focal plane and the fiducial marker focal plane at different depths relative to the objective lens.

The nature of light to be collected from the sample will depend on the type of super-resolution imaging being performed and on the nature of the sample. In some embodiments the light from the sample comprises fluorescence emitted from molecules within the sample. Such fluorescence may be generated by applying incident optical radiation to the sample at one or more wavelengths that are different from the wavelength(s) of the light to be collected from the sample for imaging purposes.

The light to be collected from the fiducial markers may arise from reflection from the fiducial markers, fluorescence within the fiducial markers or some other mechanism. The light to be collected from the fiducial markers may result when the fiducial markers are exposed to incident optical radiation. The incident optical radiation may, but does not necessarily play a role in causing emission of the light to be collected from the sample. The incident optical radiation that results in the light to be collected from the fiducial markers may have the same or different wavelength(s) as the light to be collected from the fiducial markers. Various possibilities exist for illuminating the sample and fiducial markers. These include, without limitation:

Illuminating the sample and fiducial markers with light of a first wavelength; allowing the light of the first wavelength to cause the sample to emit light of a second wavelength (either on its own or in combination with additional incident light having other properties); allowing the light of the first wavelength to reflect from the fiducial markers; collecting light of the second wavelength from the sample focal plane and collecting light of the first wavelength from the fiducial marker focal plane;

Illuminating the sample and fiducial markers with light of a first wavelength; allowing the light of the first wavelength to cause the sample to emit light of a second wavelength (either on its own or in combination with additional incident light having other properties); allowing the light of the first wavelength to cause the fiducial markers to emit light of a third wavelength (e.g. by fluorescence); collecting light of the second wavelength from the sample focal plane and collecting light of the third wavelength from the fiducial marker focal plane;

Illuminating the sample and fiducial markers with light of a first wavelength and light of a fourth wavelength; allowing the light of the first wavelength to cause the sample to emit light of a second wavelength (either on its own or in combination with additional incident light having other properties); allowing the light of the fourth wavelength to reflect from the fiducial markers; collecting light of the second wavelength from the sample focal plane and collecting light of the fourth wavelength from the fiducial marker focal plane; and Illuminating the sample and fiducial markers with light of a first wavelength and light of a fourth wavelength; allowing the light of the first wavelength to cause the sample to emit light of a second wavelength (either on its own or in combination with additional incident light having other properties); allowing the light of the fourth wavelength to cause the fiducial markers to emit light of a third wavelength (e.g. by fluorescence);

collecting light of the second wavelength from the sample focal plane and collecting light of the third wavelength from the fiducial marker focal plane.

One aspect of the invention provides a method for imaging a sample, comprising: (a) providing one or more fiducial markers near the sample; (b) imaging the sample using a first imaging system comprising an objective lens; (c) and while imaging the sample: (d) imaging the one or more fiducial markers with a second imaging system by way of the objective lens; (e) processing images of the one or more fiducial markers obtained by the second imaging system to yield a measure of drift of the fiducial markers relative to the objective lens; and (f) controlling an actuator to correct for the drift.

In some embodiments, the method additionally comprises illuminating the sample and fiducial markers using light emitted from one or more lasers.

The actuator may comprise a piezoelectric actuator operative to independently control the position of the sample relative to the objective lens in two dimensions orthogonal to an optical axis of the objective lens.

In some embodiments, the first and second imaging systems are sensitive to different light wavelength characteristics.

The method may additionally comprise imaging the sample in a different focal plane than the focal plane of the fiducial markers, and independently focusing the first and second imaging systems.

The method may automatically focus on and image the fiducial markers.

In some embodiments, an asymmetrical optical element is provided in the imaging path of the second imaging system, and processing images of the one or more fiducial markers may comprise determining a distortion in the images of the fiducial markers due to astigmatism and determining a component of the drift in a direction along a z-axis parallel to an optical axis of the objective lens based on the distortion. The asymmetrical optical element may comprise, for example, a cylindrical lens, or a pair of concave and convex cylindrical lenses. Determining the distortion may comprise determining an aspect ratio of height to width in images of the fiducial markers, and operating the actuator in response to the determined aspect ratio.

In some embodiments, a plurality of fiducial markers is provided, and imaging the fiducial markers may involve averaging the drifts of each of the plurality of markers. Averaging the drifts may comprise eliminating one or more outliers.

The method may additionally comprise obtaining multiple images of the sample.

In some embodiments, detecting light from the sample comprises detecting light emitted by fluorophores within the sample.

In some embodiments, the first and second light sensors are provided by different areas of a single imaging sensor. The Imaging sensor may be a CCD array.

Some embodiments image the sample using one of a variety of microscopy imaging techniques, including but not limited to: STED, RESOLFT, SSIM, STORM, SIM and PALM techniques.

In some embodiments, an electrically tunable lens (ETL) is used in an optical path of the second image sensor to enable the first image sensor and the second image sensor to independently focus at different focal planes. Using an ETL may extend the depth of field of the objective lens, and allows for decoupling focal planes of the first and second image sensors.

Some embodiments comprise gradually or stepwise increasing one or more of: an exposure time; a gain of the second imaging system; and an intensity of the light source that illuminates the fiducial markers over the course of acquiring a super-resolution image. This may be done to compensate for photo-bleaching of the fiducial markers for example.

In some embodiments, the first and second imaging systems comprise a single CCD, and imaging the sample comprises alternating the focus of the imaging system between the fiducial markers and the sample.

In certain embodiments, the invention provides a method of stabilizing an image generated by an optical microscope. The method comprises: (a) applying one or more light sources to a sample and a fiducial element held on a nanopositioning stage, the sample comprising a target element affected by a positional drift; (b) detecting photons emitted from the fiducial element and the target element, wherein the photons emitted by the fiducial element and the target element are detected by independent image sensors; (c) using an asymmetrical optical element such as a cylindrical lens to introduce an astigmatic effect to locate the three-dimensional (3D) position of the fiducial markers; and (d) correcting the 3D positional drift of the sample using an algorithm configured to calculate the location of the fiducial element and applying closed-loop feedback control by way of a nanopositioning stage, thereby stabilizing the sample.

In one aspect of the invention the target element and the fiducial element are separated in space along the path of the optical axis/z-direction.

In another aspect of the invention the image is a two dimensional (2D) or 3D image and is stabilized in all three dimensions to produce a drift free image.

In another aspect of the invention the nanopositioning stage is a three-axis nanopositioning stage used for positional feedback.

The sample being imaged may be substantially 2D or 3D. The sample may comprise a biological cell. The sample may incorporate the fiducial element(s).

In some embodiments, the fiducial element is affixed to or is part of the sample.

In another aspect of the invention the sample drift is corrected to less than about 50 nm in at least one direction. In yet a further aspect of the invention the sample drift is corrected to less than about 10 nm in one, two, or three axes. In yet a further aspect of the invention the sample drift is corrected to less than about 3 nm in one, two, or three axes. In yet a further aspect of the invention the sample drift is corrected to less than about 1 nm in at least one direction.

In some embodiments of the invention the sample drift is corrected to less than about 2 nm in the X and/or Y direction and less than 5 nm in the Z direction. In some embodiments of the invention sample drift is corrected to less than about 1 nm in the X and/or Y direction and less than 2.5 nm in the Z direction. Some embodiments stabilize sample drift for periods of at least several minutes. For example, some embodiments stabilize sample drift for about one hour or longer.

In yet a further aspect of the invention, a method of stabilizing an image generated by an optical microscope is provided comprising: (a) applying a light source to a sample and a fiducial element held on a nanopositioning stage, the sample comprising a target element and having a positional drift; (b) detecting photons emitted from the fiducial element with a first image sensor; (c) detecting photons emitted from the target element with a second image sensor; and (c) correcting the positional drift of the sample using an algorithm configured to calculate the location of the fiducial element and having closed-loop feedback control of the nanopositioning stage, thereby stabilizing the image.

In one aspect of this invention a relay lens is used in the optical path of the first image sensor to enable the first image sensor and the second image sensor to independently focus at different focal planes. Using this method the image of the target element on the second image sensor is brought into focus and a relay lens may be used to bring the image of the fiducial element into focus on the first image sensor. Alternately, the image of the fiducial element may be brought into focus on the first image sensor and a relay lens may be used to bring the image of the target element into focus on the second image sensor.

A further aspect of the invention provides a super-resolution microscopy system. The system comprises: (a) an objective lens; (b) a stage; (c) a first imaging system operative to image a sample on the stage by way of the objective lens; (d) a second imaging system operative to image one or more fiducial markers on the stage by way of the objective lens; (e) one or more actuators connected to move the sample relative to the objective lens; and (f) a controller comprising a processor configured to process image data from the second imaging system to determine a drift of the one or more fiducial markers and to control the one or more actuators to compensate for the drift; (g) wherein the first and second imaging system are separately focusable. The system may additionally comprise an imaging light sensor, a wavelength selector arranged to direct light having selected wavelength characteristics to the imaging light sensor and an adjustable focusing element between the wavelength selector and the imaging light sensor.

Another aspect of the invention provides a system for stabilizing an image generated by an optical microscope comprising: (a) one or more light sources configured to provide light to a sample and a fiducial element held on a nanopositioning stage, the sample comprising a target element and having a positional drift; (b) a first image sensor, configured to detect photons emitted by the fiducial element; (c) a second image sensor, configured to detect photons emitted by the target element; and (d) a computer comprising an algorithm configured to calculate the location of the fiducial element and having closed-loop feedback control of the nanopositioning stage, thereby stabilizing the image of the optical microscope.

Another aspect of the invention provides a system for stabilizing an image generated by an optical microscope comprising: (a) a first light source configured to provide light to a sample, the sample comprising a target element and having a positional drift; (b) a second light source configured to provide light to a fiducial element held on a nanopositioning stage; (b) a first image sensor, configured to detect photons emitted by the fiducial element; (c) a second image sensor, configured to detect photons emitted by the target element; and (d) a computer comprising an algorithm configured to calculate the location of the fiducial element and having closed-loop feedback control of the nanopositioning stage, thereby stabilizing the image of the optical microscope. In some aspects of the invention the first light source and the second light source emit light at different wavelengths so as to selectively stimulate fluorescence of the target element and the fiducial element at different wavelengths. In certain aspects of the invention the light from the first light source and the second light source is separated by use of a dichroic mirror. In one embodiment of this system a relay lens is positioned between the dichroic mirror and the first image sensor, such that the relay lens can adjust the focal plane of the first image sensor independently from that of the second image sensor. Alternatively, the relay lens may be positioned between the dichroic mirror and the second image sensor, such that the relay lens can adjust the focal plane of the second image sensor independently from that of the first image sensor.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1B:
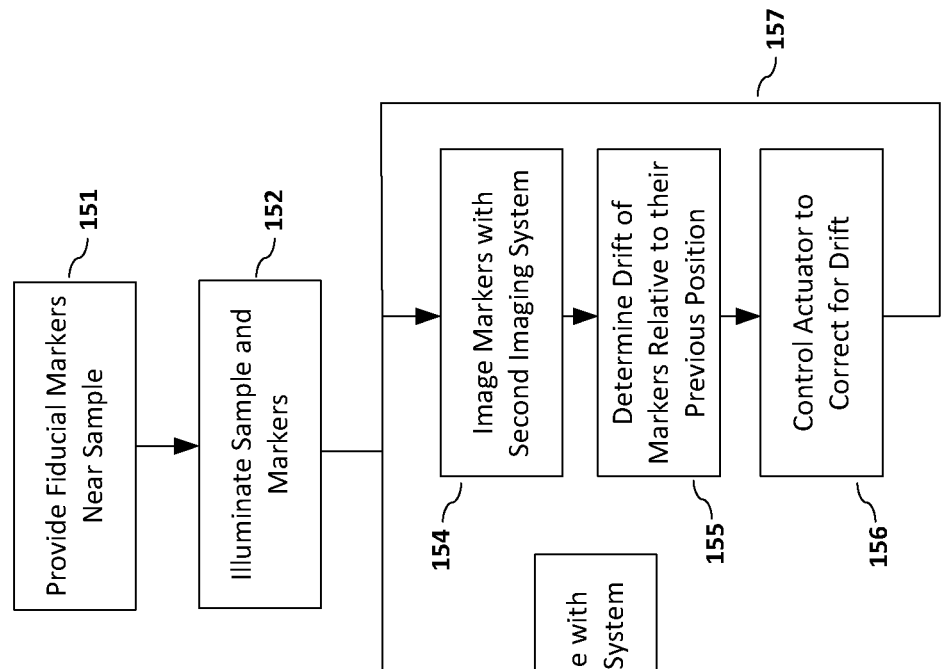
FIG. 1B is a flow chart illustrating a method for image stabilization according to an example embodiment.
Figure 1A:
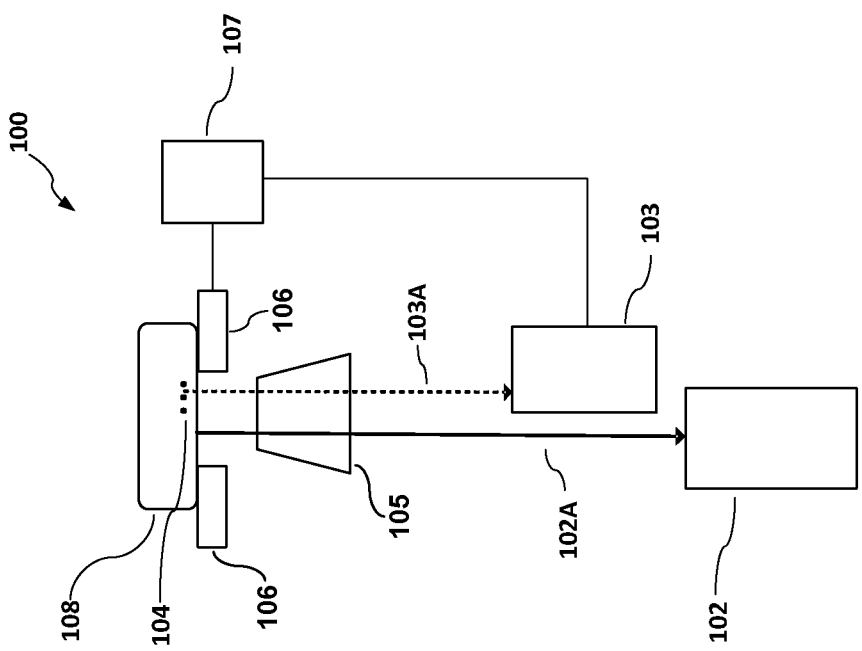
FIG. 1A is a schematic illustration of a microscope that includes an image stabilization system according to an example embodiment.

FIG. 1A is a block diagram showing a microscope 100 according to some embodiments. Microscope 100 includes first and second imaging systems 102 and 103. Imaging system 102 collects light from a sample 108 at a depth corresponding to a first focal plane FP1. Imaging system 102 may perform super-resolution imaging. Super-resolution refers to a resolution better (i.e. finer) than the resolution limit imposed by the Abbe diffraction limit.

Imaging system 103 images one or more fiducial markers 104 at a depth corresponding to a second focal plane FP2. Fiducial markers are features that may be tracked to monitor sample drift. Fiducial markers may be recognizable features on or within a sample, features built into a cover-slide or other sample support or added markers such as microbeads, nanoparticles or quantum dots. Fiducial markers may optionally be fluorescent. Fluorescent microbeads are convenient to use as fiducial markers. Fiducial markers may also be called 'fiducial elements'.

Imaging system 102 acquires light by way of an optical path 102A. Imaging system 103 acquires light by way of an optical path 103A. Optical paths 102A and 103A both pass through an objective lens 105.

Sample 108 is mounted on a stage 106 that is movable in at least two dimensions (e.g. X and Y dimensions in a plane parallel to planes FP1 and FP2). Stage 106 is optionally movable in three dimensions (e.g. the X and Y dimensions and a Z dimension perpendicular to the X and Y dimensions). Stage 106 may, for example, be controllably positioned in two or three degrees of freedom by piezoelectric actuators. Motions of stage 106 are controlled by a stage controller 107.

Imaging system 103 is configured to track motions of fiducial marker(s) 104 and to provide feedback signals to stage controller 107 that cause stage 106 to move in a way that compensates for the observed motions.

Microscope 100 does not require that any fiducial markers 104 be within the field of view of first imaging system 102. In some embodiments focal planes FP1 and FP2 are separated by a distance that is greater than a depth of field provided by objective lens 105.

FIG. 1B is a flow chart illustrating an example image stabilization method. Block 151 provides fiducial markers. Fiducial markers may, for example, comprise fluorescent microbeads and block 151 may comprise allowing the microbeads to adhere to a coverslip.

In block 152 the sample and fiducial markers are illuminated. Illumination may be by light of one or more wavelengths. In block 153 light from the sample is collected using an optical system focused at a first focal plane. The light from the sample may comprise fluorescence light emitted as a result of the illumination provided in block 152.

Blocks 154, 155 and 156 are arranged to provide a real-time drift compensation loop 157. In block 154 light from the fiducial markers is collected using an optical system focused at a second focal plane. The optical system used to collect the light from the fiducial markers may be different from or the same as the optical system used to collect light from the sample in block 153.

In block 155, images acquired in block 154 are processed to determine drift of the fiducial markers. The processing may, for example, determine a location of one or more fiducial markers and compare that location to a previous location of the same fiducial marker (e.g. a previous location determined in a prior iteration of loop 157). In an example embodiment positions of one or more fiducial markers are compared to positions of the same fiducial marker(s) determined in a first iteration of block 155.

In block 156 one or more actuators are controlled to move the sample and fiducial markers to compensate for the drift determined in block 155. In some embodiments block 154 measures drift along each of a plurality of axes and block 155 controls a corresponding plurality of actuators to move the sample along each of the plurality of axes by an amount sufficient to compensate for the drift. In some embodiments loop 157 repeats at a rate of at least a few Hz.

Figure 1C:
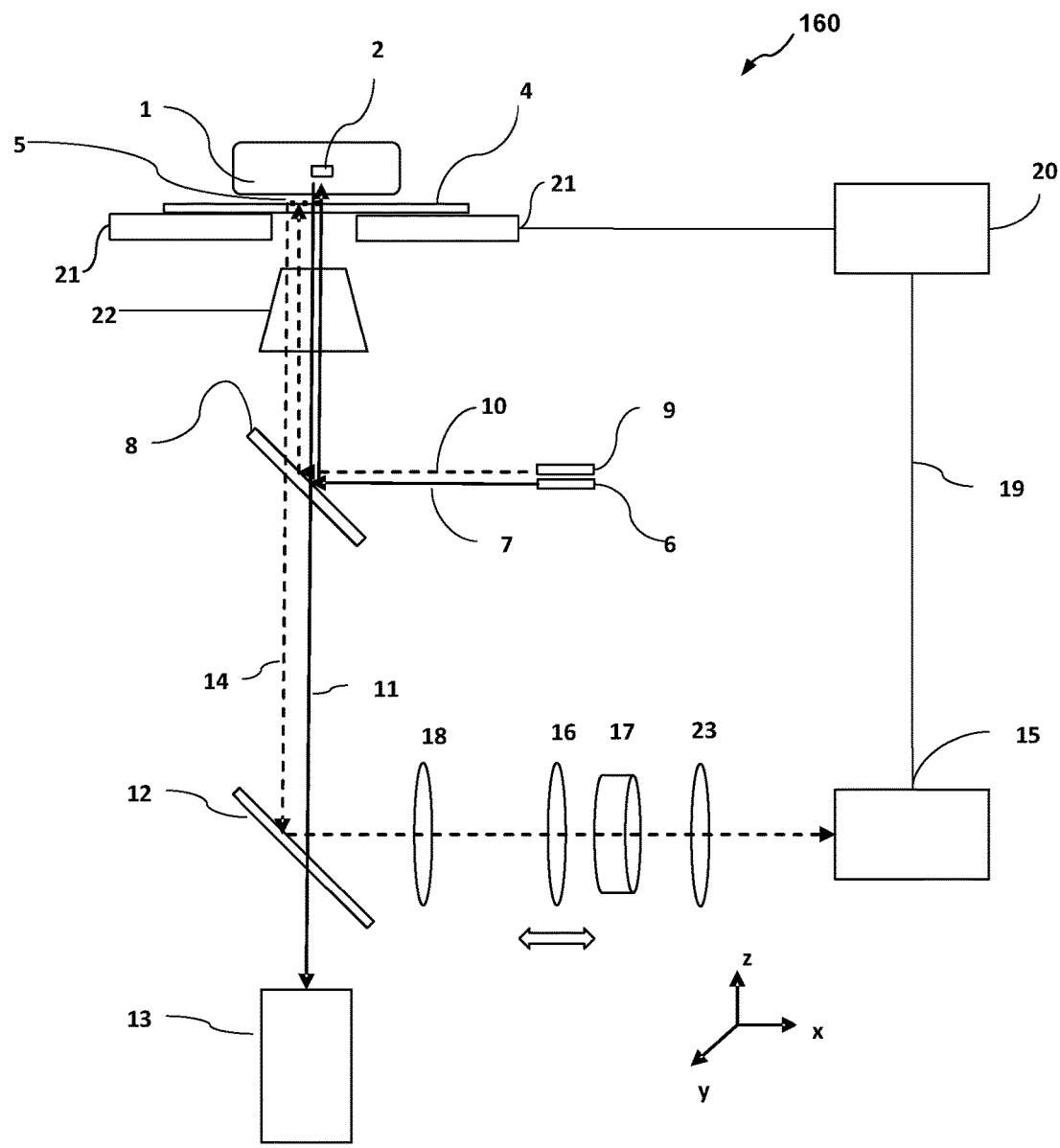
FIG. 1C is a schematic illustration of a microscope according to a simple example embodiment.

FIG. 1C shows a microscope 160 according to a simple embodiment of the invention. Sample 1 contains a target element 2 which is of interest for optical imaging. Sample 1 is placed on a suitable transparent substrate such as a microscopy coverslip 4.

Fiducial markers 5 are present, and may optionally be affixed to coverslip 4.

Coverslip 4 is supported by a nano-positioning stage 21 that is capable of controlled movement in three-dimensions with nanometer precision.

A first light source 6 provides light 7 that is directed via dichroic mirror 8 to illuminate target element 2.

A second light source 9 provides light 10 that is directed via dichroic mirror 8 to illuminate fiducial element 5.

Light 11 that may be reflected or emitted or fluoresced from target element 2 is directed by dichroic mirrors 8 and 12 to a sensor 13. Sensor 13 may for example be a camera. In some embodiments sensor 13 comprises a CCD camera.

Light 14 that may be reflected or emitted or fluoresced from fiducial element 5 is directed by dichroic mirrors 8 and 12 to a sensor 15. Sensor 15 may for example be a camera. In some embodiments sensor 15 comprises a CCD camera.

Light 14 is passed through a relay lens assembly 16 and 23, a tube lens 18 and an asymmetrical lens such as a cylindrical lens assembly 17. Cylindrical lens assembly 17 forms astigmatically aberrated images of the fiducial elements 5 on sensor 15. The astigmatically aberrated images may be processed to measure drift of the fiducial elements in a Z dimension parallel to an optical axis of objective lens 22. In this manner 3D positions of fiducial markers 5 can be established. The positions of fiducial markers 5 so calculated can be used in a closed feedback loop 19 to direct nano-positioning stage controller 20 to move nanopositioning stage 21 and thereby correct for drift of the sample 1 in the X, Y, and Z directions.

Images of target element 2 captured by sensor 13 may be brought into focus using objective lens 22. An image of fiducial markers 5 computed by sensor 15 can then be brought into focus by adjusting relay lens 16. This enables in-focus images of both the target element 2 and the fiducial markers 5 to be captured even though target element 2 and fiducial markers 5 may be relatively widely separated in the Z direction.

Sample 1 may for example comprise a biological cell.

Figure 1D:
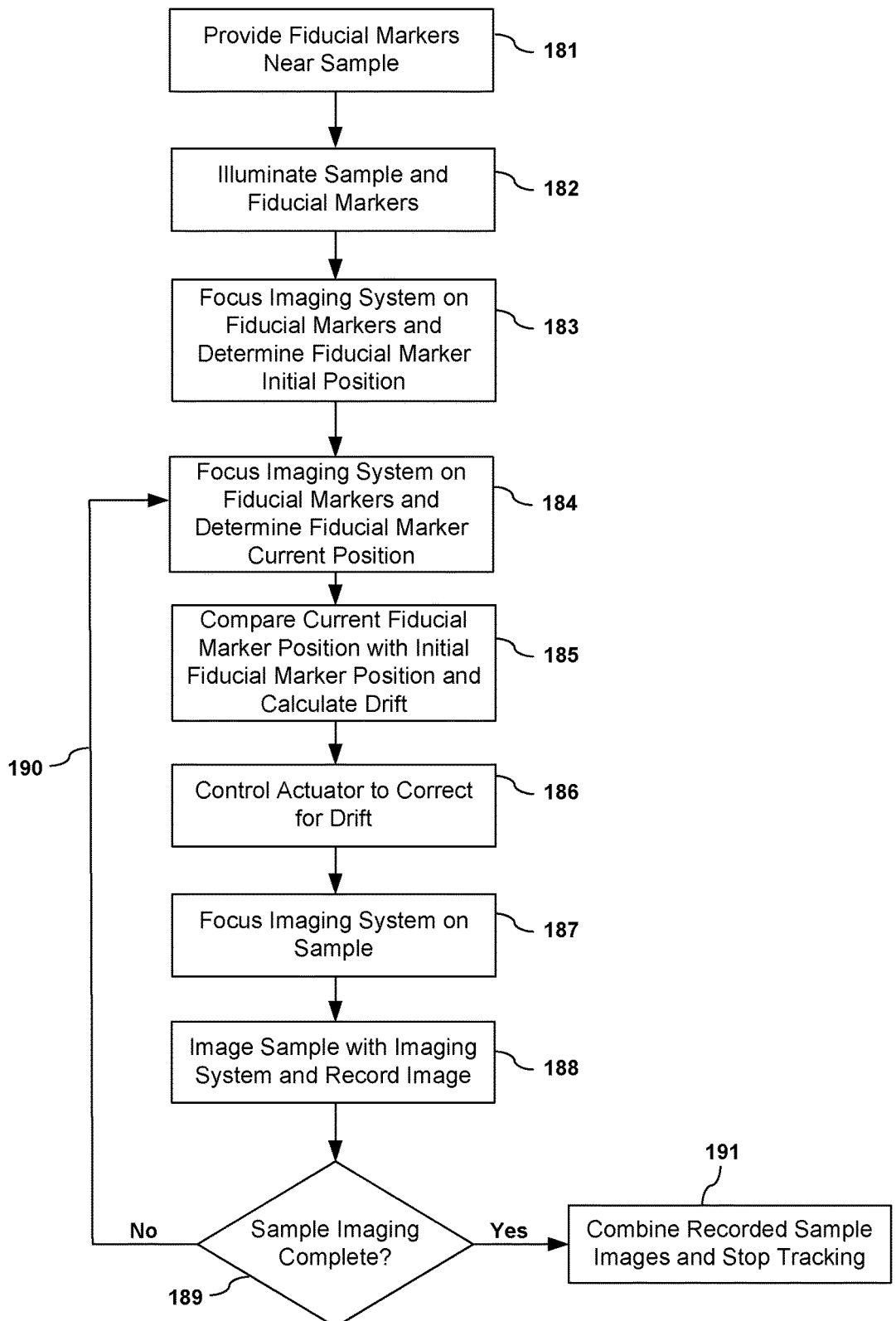
FIG. 1D is a flow chart illustrating a method for image stabilization according to another example embodiment.

FIG. 1D is a flow chart illustrating another example image stabilization method. Block 181 provides fiducial markers. In some embodiments block 181 comprises allowing fiducial markers to adhere to a coverslip.

In block 182 the sample and fiducial markers are illuminated. Illumination may be by light of one or more wavelengths. In block 183 an imaging system is focused on a fiducial marker plane, and the initial position of one or more fiducial markers is determined. In block 184 the imaging system is focused on the fiducial markers, and their current position is determined. In block 185 the current position of the fiducial marker(s) is compared to their initial position(s), and a drift of the fiducial markers is calculated.

In block 186 an actuator is controlled to correct for the drift.

In block 187 the imaging system is focused on a sample plane, and in block 188 the sample is imaged and the image is recorded. The light from the sample may comprise fluorescence light emitted as a result of the illumination provided in block 182.

In block 189, the method determines if the sample imaging is complete. If so, the method proceeded to block 191 and processes the recorded sample images. If imaging is not complete, the method repeats block 184 through to 188, until sample imaging is complete.

Figure 2A:
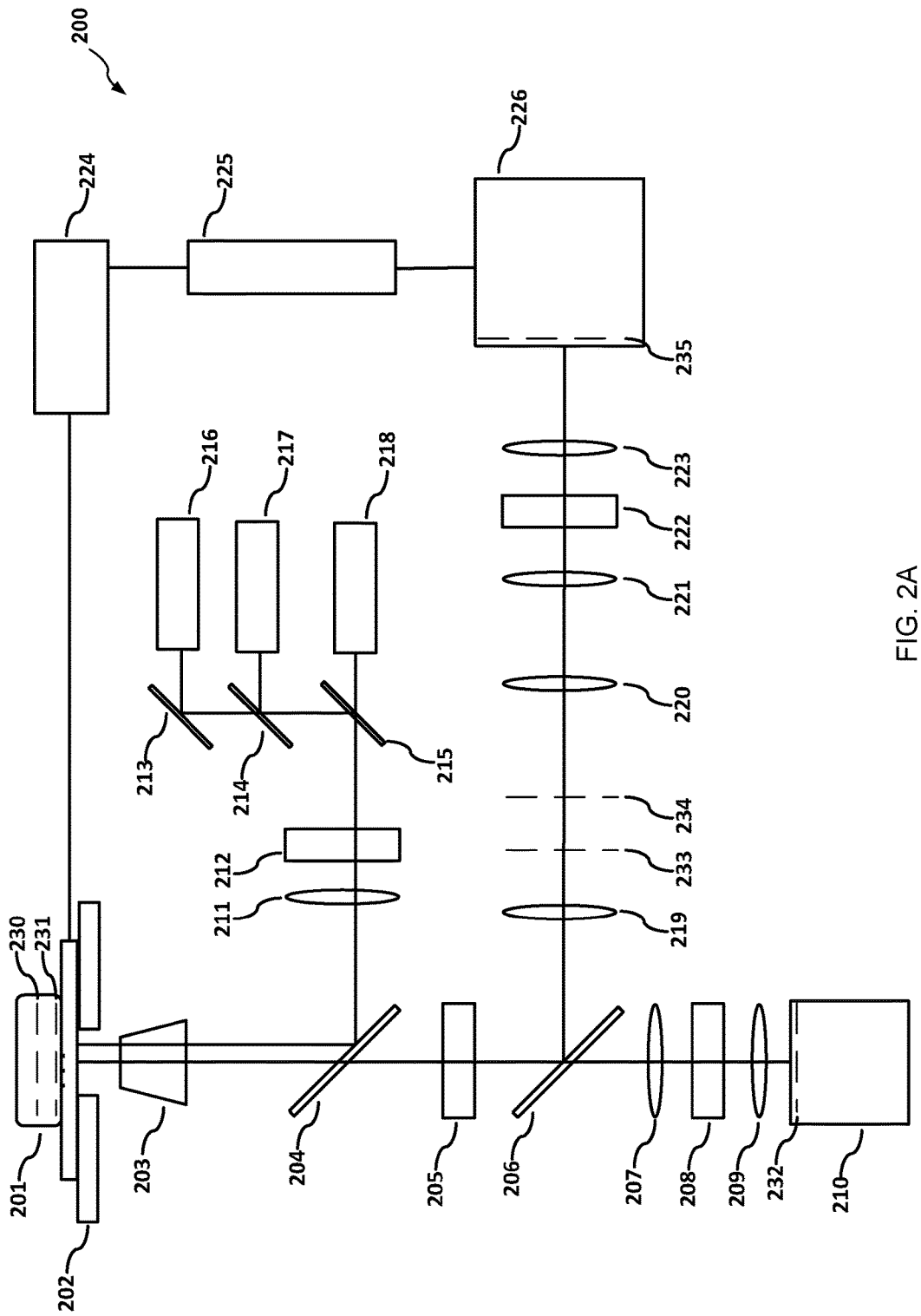
FIG. 2A is a schematic illustration showing optical paths in a microscope according to another example embodiment.

FIG. 2A shows another example microscopy system 200 in which focal planes of the sample (target element) and fiducial marker(s) (fiducial element(s)) are decoupled so that imaging and tracking of the fiducial markers are independent of the depth at which the sample is being imaged.

In system 200, sample 201 is imaged to CCD1 210, and fiducial markers are relayed to a separate camera CCD2 226. If the sample imaging depth is changed, the position of the relay imaging lens 220 may be adjusted to keep the fiducial markers in focus on CCD2 226. An astigmatism introduced into the optical path of the fiducial markers by compact lens 221 allows for precise 3D localization of the fiducial marker(s). Information regarding changes in the positions of the fiducial marker(s) is used to stabilize the sample position via a feedback loop 225.

The sample and fiducial markers are illuminated by light of one or more wavelengths. As a result the sample and fiducial markers each emit light (by reflecting the incident light, fluorescing or some other mechanism). The light emitted by the sample is separable from the light emitted by the fiducial markers (e.g. the sample emits light of a first one or more wavelengths and the fiducial markers emit light of a second one or more wavelengths distinct from the first one or more wavelengths).

System 200 illustrates the possibility that light of different wavelengths may be applied to illuminate the sample and fiducial markers. In the illustrated embodiment illumination by two wavelengths causes the sample to emit light of a third wavelength (e.g. by exciting fluorescence in fluorophores of the sample). Illumination at a fourth wavelength causes the fiducial markers to emit light of a fifth wavelength (e.g. by exciting fluorescence in the fiducial markers).

In the illustrated embodiment a 635 nm laser 218 is used for exciting fluorophores in the sample, and a 405 nm laser 217 for re-activation. A 532 nm laser 216 is used for exciting the fiducial markers. Light from the lasers is combined using dichroic mirrors 214 and 215, circularly polarized by a quarter-wave plate ($\lambda/4$) 212, and focused and directed into the back aperture of objective lens 203.

Fluorescence collected by objective lens 203 is filtered using a notch filter 205 and split by dichroic mirror 206. In the fiducial marker tracking path, a relay lens assembly 220 and 223 transfers the image of fiducial markers (e.g. beads) into camera CCD2 226. A cylindrical lens assembly 221 introduces astigmatism enabling the 3D positions of the fiducial markers to be determined. Positions of the fiducial markers in the images are used in a closed feedback loop for 3D stabilization of the microscope stage. 231, 234 and 235 indicate the focal plane of the fiducial markers on CCD2 226.

A cylindrical lens assembly 207 and a tube lens 209 are used to form astigmatically aberrated images of fluorophores in the sample onto CCD1 210. 230, 232 and 233 indicate the focal plane of the sample on CCD1 220.

If the imaging depth of the sample is changed on CCD1 210, the position of relay lens assembly 220 may be adjusted to refocus the fiducial markers on CCD2 226. The fluorescent signals from the sample and fiducial markers respectively pass through band-pass filters 208 and 222 before entering CCD cameras 210 and 226.

Figure 2B:
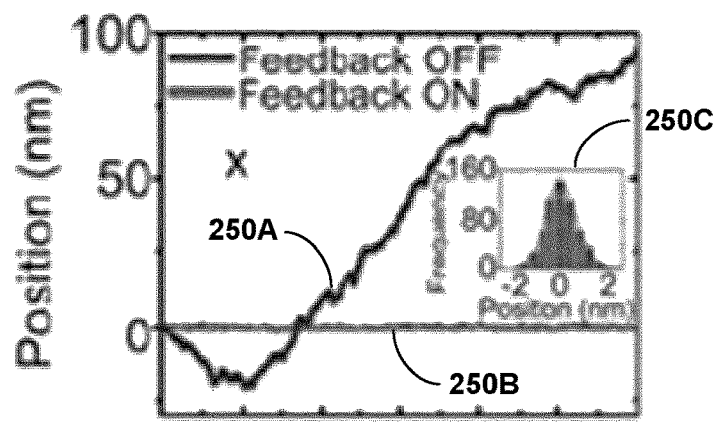
FIGS. 2B, 2C and 2D are respectively graphs showing position over time with and without stabilization along X, Y and Z axes together with histograms indicative of the performance of the real-time 3D stabilization
Figure 2C:
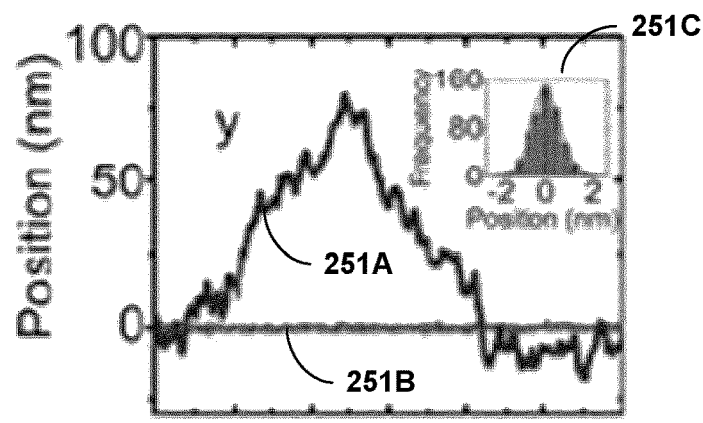
Figure 2D:
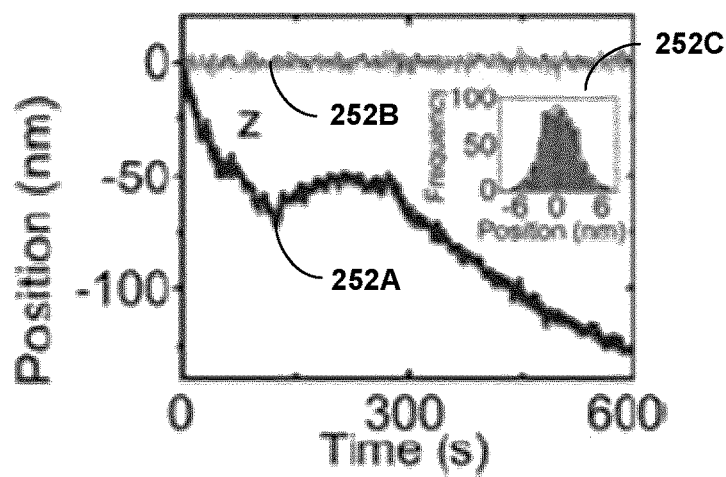

FIGS. 2B, 2C and 2D respectively indicate the positions of the fiducial markers imaged using CCD1 in X, Y and Z axes in a prototype embodiment of the invention. Curves 250A, 251A and 252A show the position of the fiducial markers without stabilization feedback. Curves 250B, 251B and 252B show the positions of the fiducial markers with stabilization feedback.

Without stabilization feedback, sample drifts in the range of a few hundred nm over a period of 10 min are typical. With real-time 3D drift correction, the sample drift is limited to 0.7 nm (rms) in X (curve 250B) and Y (curve 251B) and 2.5 nm (rms) in Z (curve 252B).

Histograms 250C, 251C and 252C show the positional stability in each direction. The standard deviations are 0.7 nm in Y, 0.7 nm in Y and 2.6 nm in Z.

Figure 3:
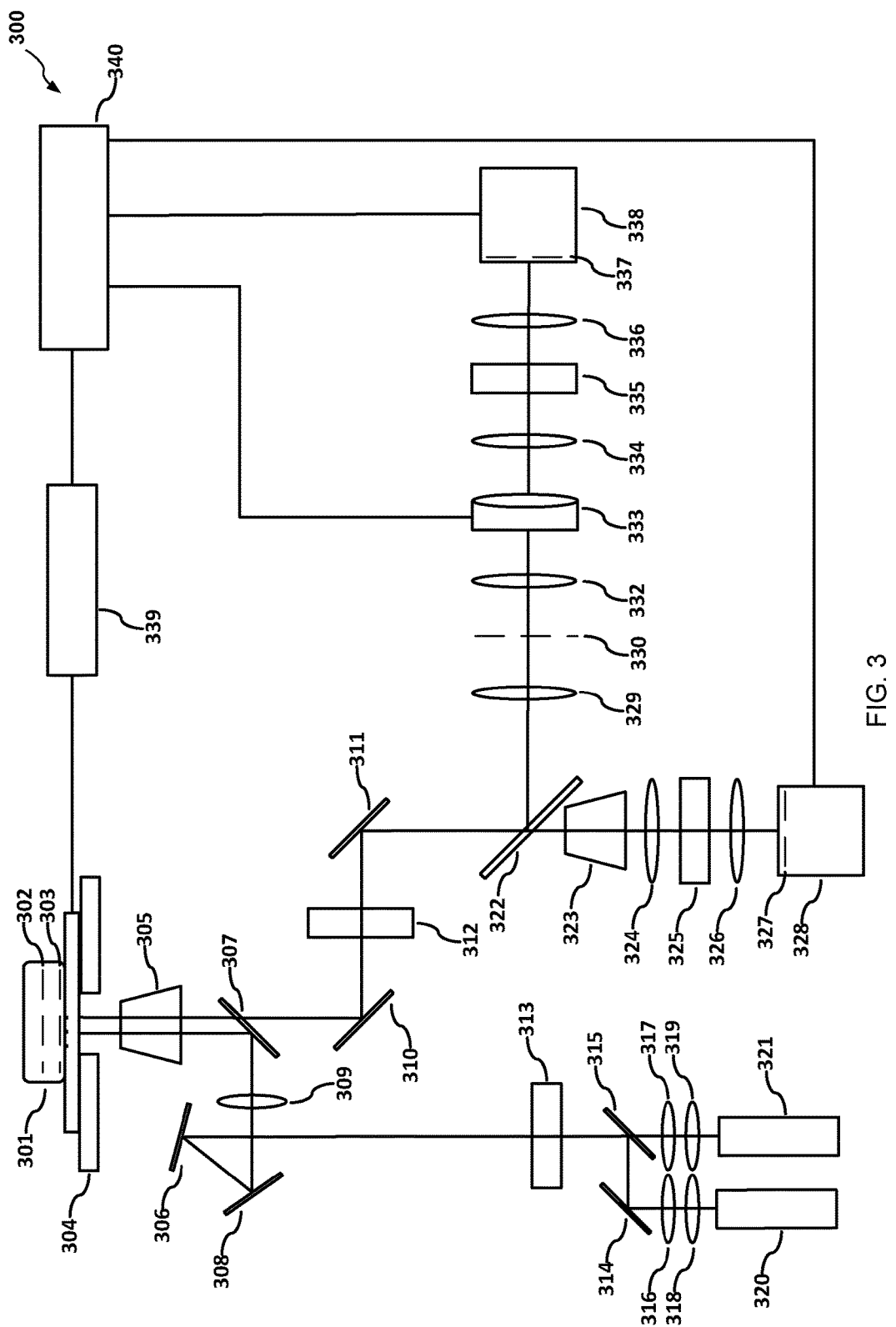
FIG. 3 is a schematic illustration showing a layout for a microscope according to an embodiment that includes an electrically tunable lens.

Some embodiments provide electronically tunable lenses (ETL) for varying depths of a sample focal plane and/or a fiducial marker focal plane. FIG. 3 is schematic illustration showing a layout of an imaging system 300. Imaging system 300 comprises an ETL that may be controlled to maintain fiducial markers in focus. In some embodiments the ETL is controlled automatically to keep the fiducial markers in focus.

In system 300 light of the same wavelength excites both fluorophores in the sample and the fiducial markers. For example, a 639 nm laser 321 may be used for excitation of fluorophores and fiducial markers and a 405 nm laser 320 may be used for reactivation of the fluorophores in the sample.

The diameters of the laser beams are adjusted using relay lenses 316, 317, 318 and 319. Beams from lasers 320 and 321 are combined using a dichroic mirror 315, circularly polarized by a quarter-wave plate 313, focused by a plano-convex lens 309 and directed into the back aperture of objective lens 305. Mirrors 306 and 308 along with plano-convex lens 309 are positioned on a translation stage (not shown) to control an incidence angle of the excitation light.

A 3D piezo stage 304 controlled by a controller 339 is connected in a feedback mechanism loop 340.

Fluorescence collected by objective lens 305 is separated by dichroic mirror 307 and filtered using notch filter 312. The fluorescence signals from the sample and the fiducial markers are separated using dichroic mirror 322. The fluorescence signals respectively pass through band-pass filters 325 and 335 before entering CCD 328 and 338.

In the fiducial marker tracking path fluorescence light passes through a relay system comprising tube lens 329 and relay lens 332. An electrically tunable lens 333 extends the depth of field of objective lens 305 and refocuses the image of the fiducial marker(s) on CCD 338 even when imaging many micrometers deep within a sample.

A cylindrical lens assembly 334 is composed of a plano-convex and a plano-concave round cylindrical lens introduces astigmatism into the detection path, enabling the 3D positions of the fiducial markers to be determined. These positions are used in a closed feedback loop for 3D stabilization of stage 304.

Cylindrical lens assembly 324 and tube lens 326 are used to form astigmatically aberrated images of the fluorophores in the sample onto EMCCD 328. 2.5× zoom lens 323 is used to obtain an appropriate magnification of 150× on EMCCD 328. Focal plane 302, 327 and 330 of the structure of interest is focused on EMCCD 328, and focal plane 303 and 337 of the fiducial markers is focused on CCD 338.

Figure 4E:
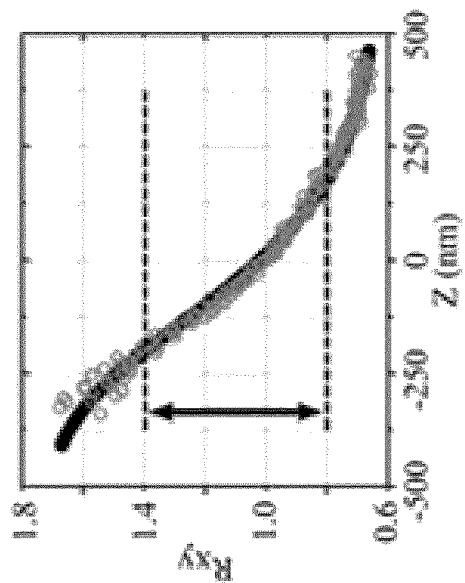
FIG. 4E is a plot of the aspect ratio of an astigmatic PSF as a function of Z displacement.
Figure 4B:
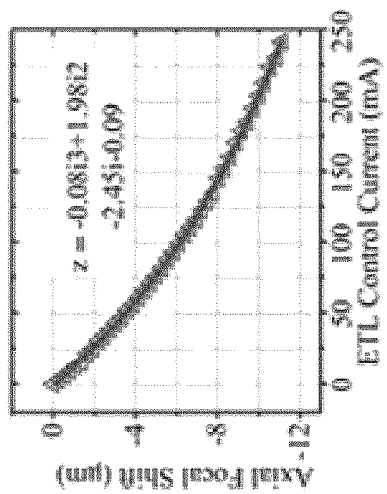
FIG. 4B is a plot of axial focus shift as a function of electrical current in an electrically tunable stabilization system.
Figure 4D:
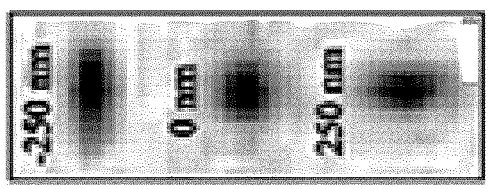
FIG. 4D shows three cross sections of an astigmatically aberrated PSF at different axial positions.
Figure 4A:
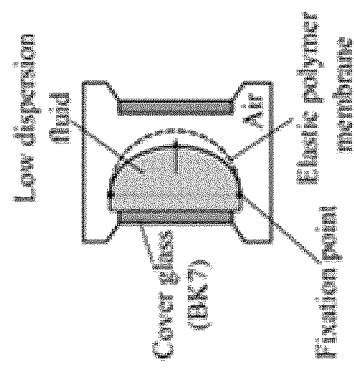
FIG. 4A is a schematic illustration of an electrically tunable lens.

FIG. 4A is a schematic depiction of an example electrically tunable lens based on shape-changing polymer membrane technology.

FIG. 4B shows axial focal shift as a function of current for an ETL used in a stabilization system.

Figure 4C:
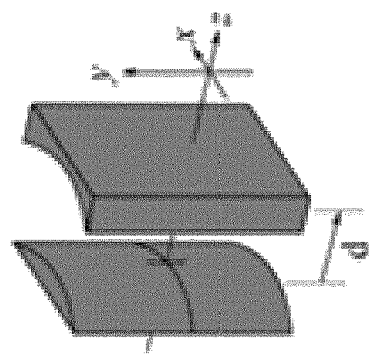
FIG. 4C is a schematic representation of a cylindrical lens that may be applied for producing an astigmatic effect.

FIG. 4C is a schematic representation of a cylindrical lens compound, which is an example of an asymmetrical optical element that may be used to introduce an astigmatic effect into the detection path of the fiducial markers.

FIG. 4D shows three x-y cross sections of an astigmatically aberrated PSF at different axial (Z-axis) positions.

FIG. 4E shows the aspect ratio ($R_{xy}$) of an astigmatic PSF as a function of Z. The black arrow shows the range of ellipticity which is used for tracking the depth (Z-axis position) of fiducial markers. This range provides sufficient sensitivity to achieve high accuracy tracking of fiducial markers in the axial direction.

Figure 5A:
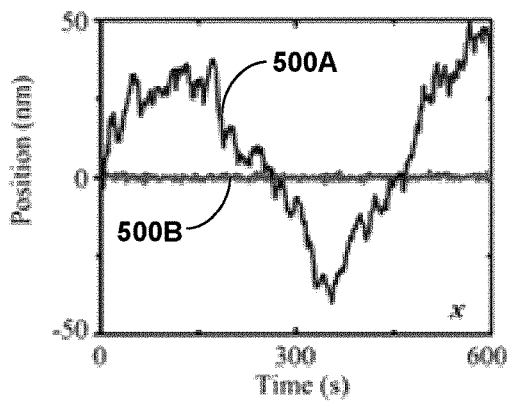
FIGS. 5A, 5B and 5C are graphs of position of fluorescent beads as a function of time with and without stabilization.
Figure 5D:
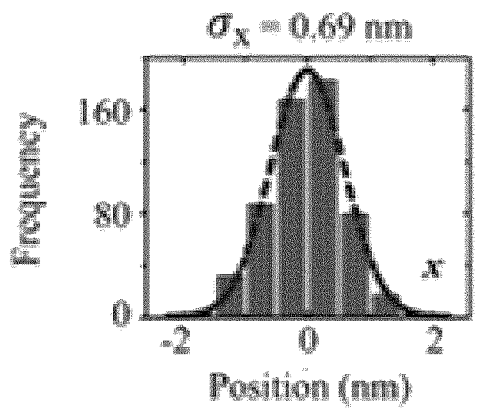
FIGS. 5D, 5E and 5F are histograms illustrating standard deviations of tracking accuracy.
Figure 5B:
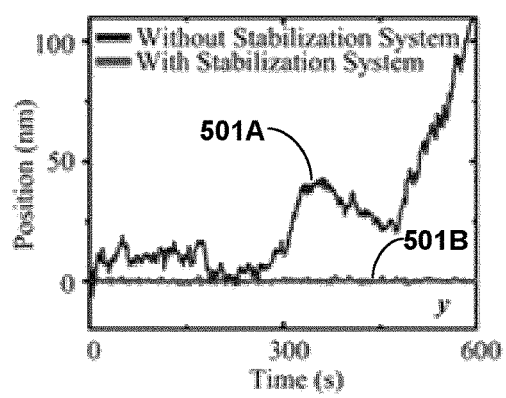
Figure 5E:
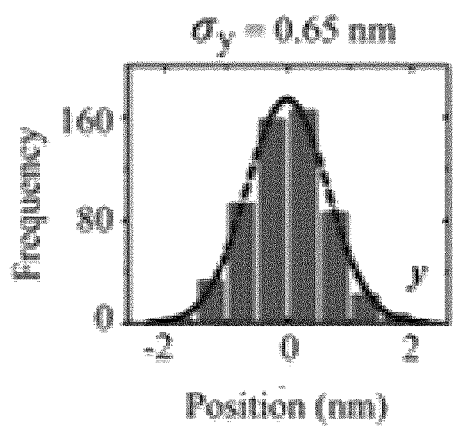
Figure 5C:
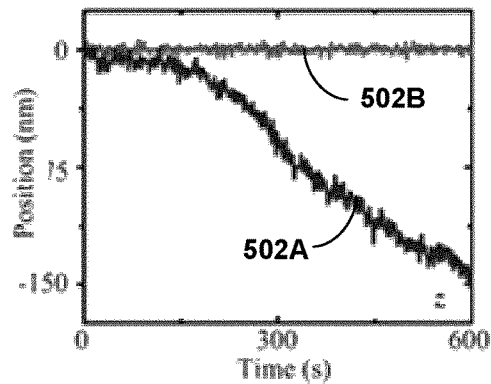

FIGS. 5A, 5B and 5C respectively show tracked positions of fluorescent beads in X, Y and Z dimensions over 10 min with the stabilization system (curves 500B, 501B and 502B) and without the stabilization system (curves 500A, 501A and 502A).

Figure 5F:
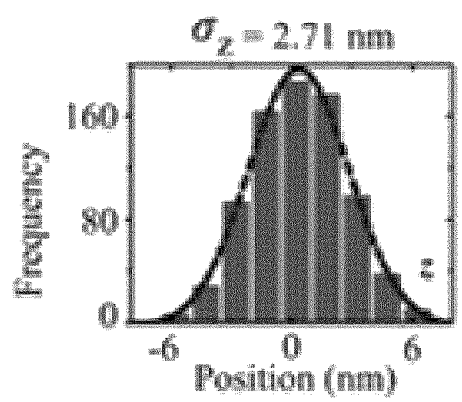

FIGS. 5D, 5E and 5F are respectively histograms of bead tracking accuracy in X, Y and Z directions. Standard deviations are 0.69 nm in X, 0.65 nm in Y and 2.71 nm in Z. Four fiducial markers on the CCD are used for stabilizing the setup. The data shown here were obtained by analyzing the stability of three TetraSpeck™ beads on the EMCCD.

Figure 6A:
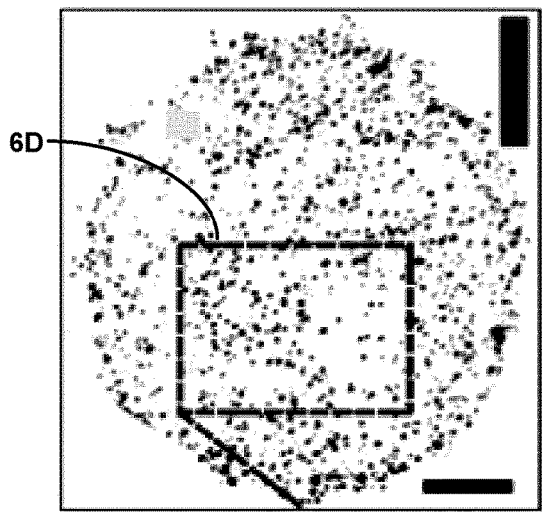
FIGS. 6A and 6B are STORM images of transferring receptors respectively obtained with and without stabilization.
Figure 6B:
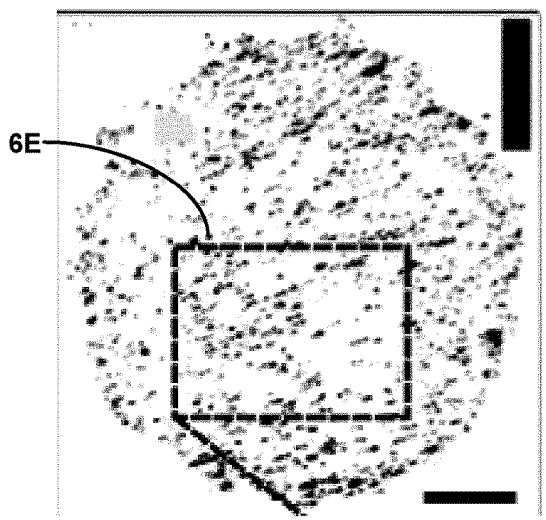

FIGS. 6A to 6L show the organization of transferrin receptors in a drift-free super-resolution image vs. a corresponding drifted image. FIG. 6A is a STORM image of transferrin receptors in a B cell, obtained with the stabilization system, and FIG. 6B is an image obtained without the stabilization system. Scale bars in both figures are 2 μm.

Figure 6C:
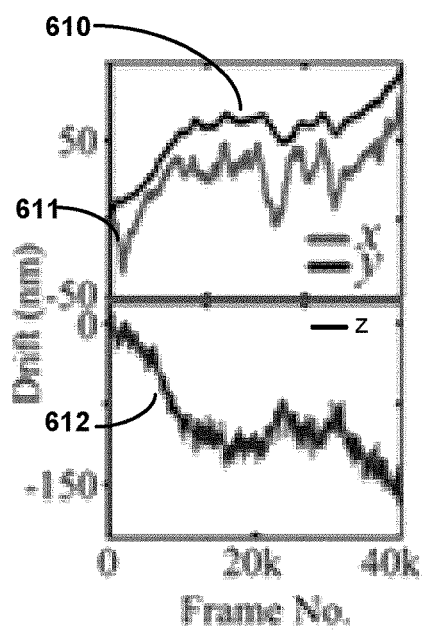
FIG. 6C is a graph showing the actual drift that occurred during STORM data acquisition for FIG. 6B.

FIG. 6C shows the actual drift in the X 611, Y 610 and Z 612 directions that occurred during STORM data acquisition.

Figure 6F:
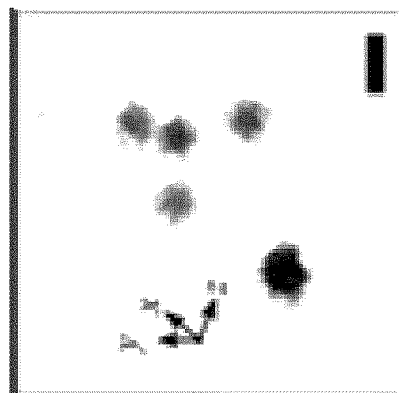
FIGS. 6F and 6G are 3D representations of regions from FIGS. 6D and 6E respectively.
Figure 6G:
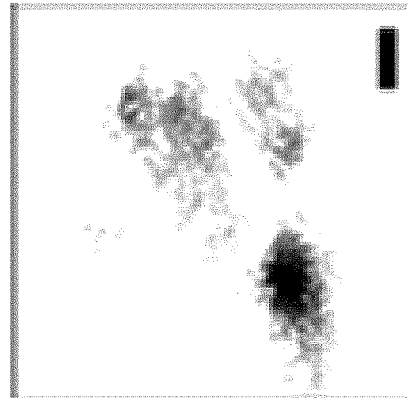
Figure 6D:
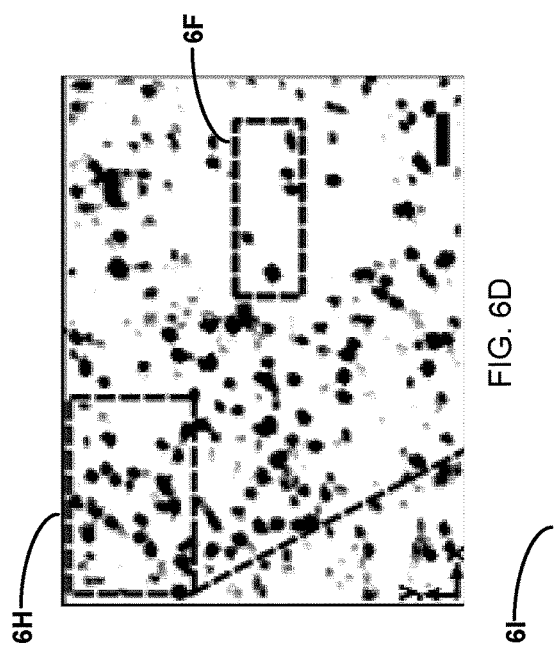
FIGS. 6D and 6E show insets of the regions from FIGS. 6A and 6B respectively.
Figure 6E:
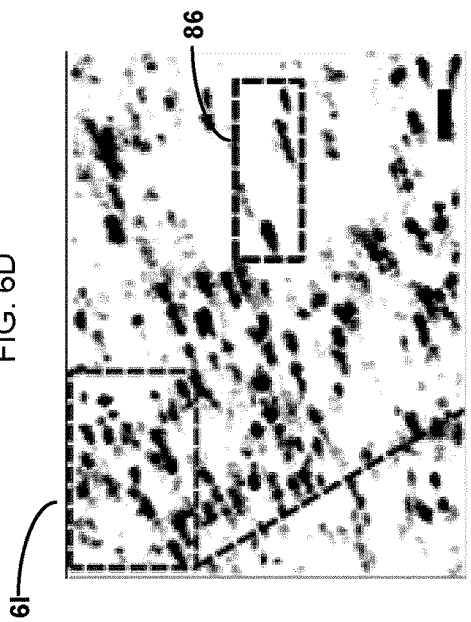

FIGS. 6D and 6E are insets of the regions marked in FIGS. 6A and 6B respectively. Scale bars in both figures are 500 nm.

Figure 6H:
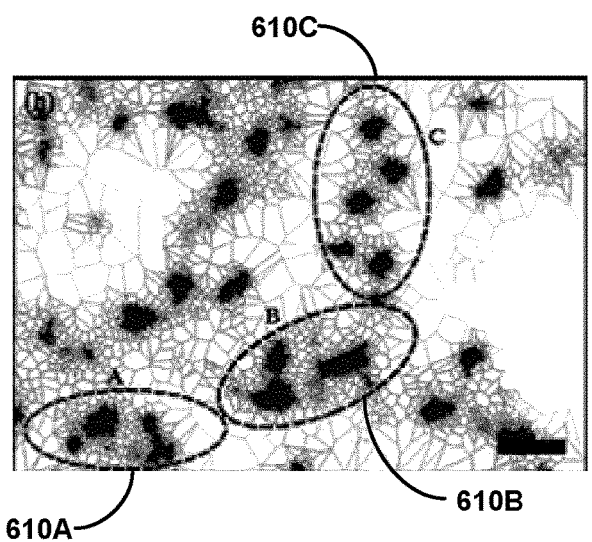
FIGS. 6H and 6I are images of transferrin clusters in the drift free and drifted images in FIGS. 6A and 6B respectively.
Figure 6I:
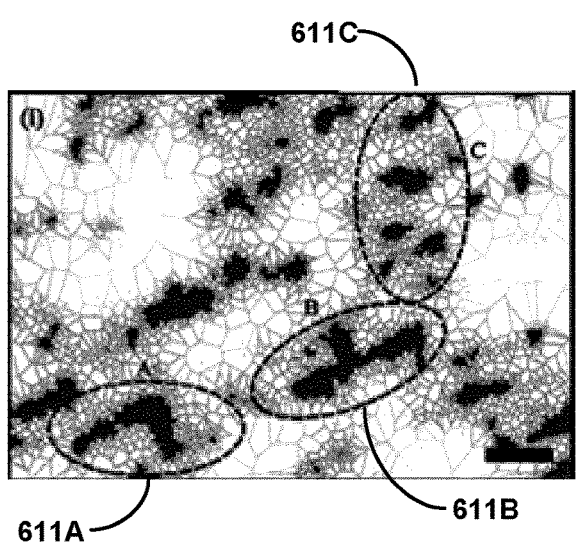

FIGS. 6F and 6G are 3D representations of the regions marked in FIGS. 6D and 6E respectively. FIGS. 6H and 6I are Voronoï tessellation maps of regions marked in Figured 6D and 6E respectively. Shaded regions show the transferrin clusters segmented using density thresholding. Scale bars in FIGS. 6F to 6I are 200 nm.

Figure 6J:
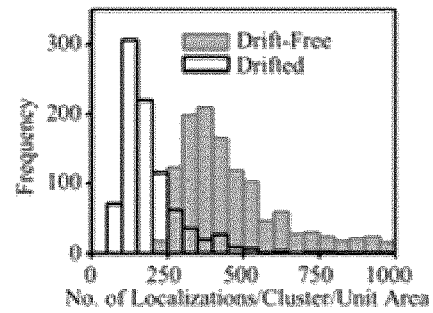
FIGS. 6J, 6K and 6L show distributions of cluster density, cluster diameter, and cluster circularity.

FIG. 6J shows the cluster density in the drift-free image and the drifted image.

Figure 6K:
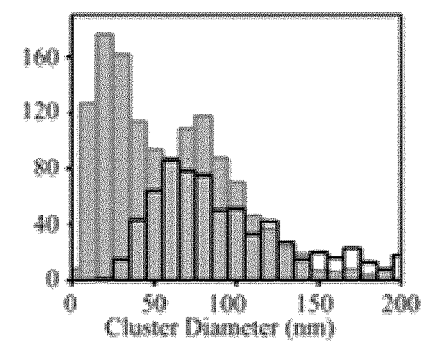

FIG. 6K shows the cluster diameter in the drift-free image and the drifted image.

FIG. 6K shows the cluster circularity in the drift-free image and the drifted image.

Example Prototype Embodiments

A first prototype embodiment was made by customizing an inverted microscope. The prototype embodiment had the optical arrangement shown in FIG. 2A. The microscope was equipped with an apochromatic TIRF oil-immersion objective lens (60×; NA 1.49; Nikon Instruments, Melville, N.Y.).

Separate illumination sources were used to cause emission of light from the target elements and to cause emission of light from fiducial markers. A 405 nm laser (Thorlabs) and a 639 nm laser (Genesis™ MX639, Coherent, Santa Clara, Calif.) were used for excitation of target elements, which may be labeled using Alexa™ 647 dye (Life Technologies, Burlington, ON).

Excitation of fiducial markers (fluorescent beads) was provided by a separate 532 nm laser (Excelsior One™, Spectra-Physics). Laser beams were collimated, combined, circularly polarized and focused into the back aperture of the objective lens.

A translational stage was used to shift the incident beam for either oblique incident excitation (deep imaging) or total internal reflection fluorescence imaging (near-surface imaging). A quad-band polychroic mirror (Di01-R205/488/532/636, Semrock) was used to reflect the excitation laser beams and transmit the fluorescence signals. A long-pass dichroic mirror (FF640-FDi01, Semrock) was utilized to separate fluorescence emission of the target element from fluorescence emissions from the fiducial markers.

In the detection path of target element, emission light passed through a cylindrical lens assembly 207, filtered by a band-pass filter (FF01-675/70, Semrock) and finally imaged to a back-illuminated CCD camera (iXon Ultra 897 BV™, Andor) using a 200 mm achromatic doublet lens (ACA254-200-B, Thorlabs). A 2.5× magnifying lens compound was placed before cylindrical lens assembly 207 to obtain an overall magnification of 150×, which corresponds to a pixel size of 100 nm on CCD1 210.

A 100 mm achromatic doublet lens (AC254-100-A, Thorlabs) was placed in the detection path of the fiducial markers. This doublet lens functions as a relay imaging lens 220. When the imaging depth is changed, the position of relay imaging lens 220 can be adjusted to keep the fiducial markers in focus on CCD2 226. A 250 mm achromatic doublet lens (AC254-250-A, Thorlabs) was used to form an image of fiducial markers at the back focal plane of relay imaging lens 220. The emission light then passed through a cylindrical lens assembly 221, filtered by a band-pass filter (FF01-562/40, Semrock) and finally imaged to CCD2 226 (Newton 970 UBV, Andor) using a 200 mm achromatic doublet lens (ACA254-200-B, Thorlabs).

Astigmatism was introduced into each optical path by, in each case, a pair of 40 mm concave and −40 mm convex cylindrical lenses. This approach provides a continuously variable astigmatic effect for obtaining the correct astigmatic effect for deep imaging.

To actively stabilize the microscope stage in 3D during the image acquisition, up to five different fiducial markers were used for tracking. Beads were subsequently fitted using an error function to determine their axial and lateral positions as follows:

$$I(x, y) = A\left(\mathrm{erf}\left(\frac{x - x_0 + 0.5}{\sqrt{2}\,\sigma_0}\right) - \mathrm{erf}\left(\frac{x - x_0 - 0.5}{\sqrt{2}\,\sigma_0}\right)\right)$$
$$\left(\mathrm{erf}\left(\frac{y - y_0 + 0.5}{\sqrt{2}\,\sigma_0}\right) - \mathrm{erf}\left(\frac{y - y_0 - 0.5}{\sqrt{2}\,\sigma_0}\right)\right) + B$$

where $I(x, y)$ is the intensity, A is the amplitude and $x_0$ and $y_0$ are the emitter positions in lateral directions. $\sigma_0$ and B are standard deviation and background noise, respectively. By taking the error-propagation-weighted average of calculated drifts for each single fiducial marker, an appropriate voltage was then sent to the piezo stage (Max311D, Thorlabs) using a 16-bit data acquisition card (PCI6323, National Instruments) and a piezo-stage controller (MDT693B, Thorlabs). Huang, F., Schwartz, S. L., Byars, J. M. & Lidke, K. A.

*Biomedical Optics Express* 2, 1377-1393 (2011) describes one example way to determine drift from images of fiducial markers.

An exposure time of ~200 ms was typically used for imaging the fiducial markers. With additional time of 1-2 ms for settling the piezo stage as well as ~10 ms for image processing and fitting, drift correction was conducted at a rate of 4-5 Hz.

To examine the performance of the active stabilization system, positional stability of 100 nm fluorescent beads on CCD1 was traced for 10 minutes. The results of this experiment are shown in FIG. 2B.

Two different types of beads were mixed and affixed to the coverslip. A mixture of 100 nm TetraSpeck™ beads (T7279; Life Technologies, Burlington ON) at a concentration of 1 in 200, and 100 nm Orange FluoSpheres™ (F8800; excitation 540 nm, emission 560 nm, Life Technologies) at a concentration of 1 in 100000 were settled onto a poly-L-lysine coverslip overnight. The coverslip was rinsed to remove any beads that had not firmly attached and then mounted using a TN buffer (50 mMTris, 10 mMNaCl, pH 8). The slide was then mounted on the microscope stage and the cameras were synchronized.

Drift correction was conducted by tracking 100 nm Orange FluoSpheres beads on CCD2. TetraSpeck beads were simultaneously tracked on CCD1 for further processing. With active stabilization engaged, beads on CCD1 were locked within a standard deviation of 0.7 nm laterally and 2.6 nm axially over 10 min. The accuracy in axial direction is worse than that in lateral directions because the axial position is deduced from widths of elliptical PSF, which leads to an error accumulation.

Second Prototype Embodiment

A second prototype embodiment used an electronically-tunable lens. The custom-built STORM system of the first prototype embodiment was modified to incorporate an electrically tunable lens 333 as shown in FIG. 3. The 639 nm laser was also used for excitation of 100 nm Infrared FluoSpheres (F8799, Life Technologies). Activation of the Alexa 647 fluorophores (i.e. increasing the transition rate of fluorophores between dark and bright states) was provided by a 405 nm laser (LRD 0405, Laserglow Technologies, Toronto, Canada).

Laser beams were collimated, combined, circularly polarized and focused onto the back aperture of the objective lens (318 and 319; AC127-030-A, 316 and 317; AC127-075-A, 315; FF560-FDi01, 313; AQWP05M-600, 309; AC254-150-A, Thorlabs, Newton, N.J.). Mirror 306 and 308 were moved by a translation stage (PT1, Thorlabs) to control incident beam angle and to switch between epi-illumination and oblique incident illumination modes.

A 3D piezo stage (Max311D, Thorlabs) equipped with a 16-bit digital-to-analog converter (PCI6323, National Instruments, Austin, Tex.) and a piezo-stage controller (MDT693B, Thorlabs) was used to locate the region of interest and stabilize the microscope during data acquisition. A quad-notch filter (312; 405/488/532/636, Semrock) was placed in the detection path to further block the excitation/activation lasers. A short-pass dichroic mirror (322; FF720-FDi01, Semrock) was used to separate the fluorescence emission of Alexa 647 from that of the fiducial markers.

The detection path of the Alexa 647 contained a weak cylindrical lens assembly (324; effective focal length (EFL) =10 m) composed of a plano-convex and a plano-concave round cylindrical lens with anti-reflection coating and focal lengths of ±400 mm (LJ1363RM-B and LK1487RM-A, Thorlabs). Cylindrical lens assembly 324 introduced astigmatism into the imaging path, creating slightly different focal planes in the X and Y directions. This resulted in elliptical PSFs for the fluorophores (i.e. the ellipticity and orientation of PSF varies along the optical axis). This allowed for the decoding of the axial positions of fluorophores within a few hundred nanometers above and below the focal plane of the objective lens 305. Concave and convex cylindrical lenses were separated by a distance, d.

The emission light was imaged to a back-illuminated electron multiplying charge-coupled device (328; iXon Ultra DU-897U, Andor, South Windsor, Conn.).

In the detection path of the fiducial markers, the emission light passed through a 250 mm achromatic doublet lens (329; AC254-250-A, Thorlabs) followed by a relay imaging lens (332; AC254-100-A, Thorlabs). An electrically tunable lens (333; EL-10-30-Ci-VIS-LD, Optotune) was placed after the relay system such that it is conjugate to the back focal plane of the objective lens. The emitted light then passed through a cylindrical lens assembly (334; EFL=2 m), which has a design analogous to that of 324; The focal lengths of the concave and convex components in 334 are ±200 mm (LJ1653RM-B, LK1069RM-A, Thorlabs). The emission light then passed through a band-pass filter (335; FF01-747/33, Semrock) and a 200 mm achromatic doublet lens (336; ACA254-200-B, Thorlabs) before being imaged by the CCD (338; Newton 970 UBV, Andor).

In order to measure the performance of the active stabilization system, a mixture of 100 nm TetraSpeck beads (T7279; Life Technologies) at a concentration of 1 in 200, and 100 nm Infrared FluoSpheres (excitation 540 nm; emission 560 nm) at a concentration of 1 in 200000 were affixed onto a poly-L-lysine-coated coverslip. The coverslip was then rinsed to remove beads that had not firmly attached and mounted in phosphate-buffered saline. The 100 nm Infrared FluoSpheres were tracked on the CCD to provide drift correction feedback. TetraSpeck beads were simultaneously imaged on EMCCD to measure the real stability of the imaging system.

Splenic B cells from 8-week old C57BL/6 mice were used. Splenic B cells were isolated, as described in S. A. Freeman, V. Jaumouillé, K. Choi, B. E. Hsu, H. S. Wong, L. Abraham, M. L. Graves, D. Coombs, C. D. Roskelley, R. Das, S. Grinstein, and M. R. Gold, "Toll-like receptor ligands sensitize B-cell receptor signalling by reducing actin-dependent spatial confinement of the receptor," Nat Commun 6, 6168 (2015), using a B cell isolation kit (#19854, Stemcell Technologies) to deplete non-B cells. To increase TfR expression levels (J. Futran, J. D. Kemp, E. H. Field, A. Vora, and R. F. Ashman, "Transferrin receptor synthesis is an early event in B cell activation," Journal of Immunology (Baltimore, Md.: 1950) 143, 787-792 (1989); L. M. Neckers, G. Yenokida, and S. P. James, "The role of the transferrin receptor in human B lymphocyte activation," Journal of Immunology (Baltimore, Md.: 1950) 133, 2437-2441 (1984)). B cells were cultured in RPMI-1640 supplemented with 10% fetal calf serum, 2 mM glutamine, 1 mM pyruvate, 50 μM 2-mercaptoethanol, 50 U/mL penicillin and 50 μg/mL streptomycin (complete medium) and stimulated with 5 μg/ml *E. coli* 0111:B4 LPS (#L2630, Sigma-Aldrich catalogue) for 12 hr, as described in B. Huang, W. Wang, M. Bates, and X. Zhuang, "Three-Dimensional Super-Resolution Imaging by Stochastic Optical Reconstruction Microscopy," Science 319, 810-813 (2008).

B cells were plated on coverslips (18 mm; #1.5H, Marienfeld,) functionalized with non-stimulatory M5/114 anti-MHCII monoclonal antibody (#12-5321, eBioscience) for 10 min at 4° C., and subsequently fixed with ice cold 4% paraformaldehyde, 0.2% glutaraldehyde in PBS for 90 min. Fixed cells were washed in PBS (3×), permeabilized with 0.1% Triton for 5 min after which they were washed in PBS again (3×). The sample was blocked in blocking buffer (10% normal goat serum in PBS) for 1 hr at 4° C. and subsequently stained with primary antibody (transferrin receptor; #13-6800, Invitrogen) overnight at 4° C. Cells were then washed in PBS (3×), incubated at room temperature for 30 min with goat anti-mouse Alexa Fluor 647 (A21244, Life Technologies) and then washed with PBS (5×) followed by a secondary fixation in 4% paraformaldehyde for 10 min and a final series of PBS washes (5×). Fluorescent fiducial markers (F8800, Life Technologies) were incubated with the sample overnight at 4° C. for the purpose of sample stabilization during image acquisition.

Imaging was performed in a standard GLOX-thiol solution (TN buffer [50 mM Tris, 10 mM NaCl, pH 8.0], 0.5 mg/ml glucose oxidase, 40 µg/ml catalase, 10% (w/v) glucose and 140 mM beta-mercaptoethanol). The coverslip along with the sample were mounted onto depression slides and sealed with the two-component silicone-glue Twinsil™ (Picodent, Wipperfürth, Germany, #13001000).

The ETL used in this prototype stabilization system functions based on the shape changing principle. It has low dispersion in the visible range (wavefront error <0.25λ) and a focal length, $f_{ETL}f_{ETL}f_{ETL}f_{ETL}$, spanning from 200 mm to 100 mm (10 mm aperture size; C-mounted). It comprises a polymer membrane surrounded with a low dispersion fluid on one side and air on the other side, as shown in FIG. 4A. The curvature of the polymer membrane increases (i.e. $f_{ETL}$ decreases) as the current applied to the ETL is increased; conversely, $f_{ETL}$ decreases by lowering the current. The whole system is trapped between two anti-reflection coated BK7 cover glasses and mounted using a stiff plastic material (G. Beadie, M. L. Sandrock, M. J. Wiggins, R. S. Lepkowicz, J. S. Shirk, M. Ponting, Y. Yang, T. Kazmierczak, A. Hiltner, and E. Baer, "Tunable polymer lens," Opt. Express 16, 11847-11857 (2008); G. Eberle, V. Chiron, and K. Wegener, "Simulation and Realization of a Focus Shifting Unit using a Tunable Lens for 3D Laser Material Processing," Physics Procedia 41, 441-447 (2013)).

A programmable lens driver equipped with a temperature sensor and a drift compensation mechanism was used to control the ETL. When the imaging depth was changed, an appropriate current was applied to the ETL to tune $f_{ETL}$ and keep the fiducial markers in focus on the CCD.

In order to characterize the dynamic behavior of the ETL, 100 nm TetraSpeck™ beads attached to the coverslip were used. Starting with the beads in focus on the CCD (i.e. when the ellipticity of the beads' PSFs=1), an appropriate voltage was applied to the piezo stage to move the sample in the Z direction. The current was then increased gradually to bring the fluorescent beads back into focus on the CCD. Knowing the actual shift of the sample in Z as well as the applied current, the relationship between the control current and the actual focal shift was obtained, as shown in FIG. 4B. Displacement of the axial focal plane ($\delta z$) was measured to be ~11 µm when the control current was increased from 0 to 250 mA. Note that the ETL must be mounted horizontally to avoid the effect of gravity on its refractive power. Vertical mounting also induces a significant comatic aberration into the detection path. The ETL should be aligned precisely to ensure that the magnification of the detection path is independent of the $f_{ETL}$. Precise alignment was achieved through an iterative process using a grid distortion test target (R1L3S3P, Thorlabs). $f_{ETL}$ was changed to its maximum and minimum values and the grid images were recorded. The ETL was aligned such that the shift between the two images was insignificant. The response time of the ETL was measured to be less than 50 ms.

The ETL was paired with a weak cylindrical lens compound (334; focal length: $f_{CL2}$) to introduce an adaptive astigmatic effect into the imaging path of the fiducial markers. Cylindrical lens 334 is composed of a plano-convex and a plano-concave round cylindrical lens with focal lengths ($f_{cl}$) of ±200 mm, separated from each other by a distance d, as shown in FIG. 4C. It is simpler and more cost effective compared to previously proposed methods based on a deformable mirror array (I. Izeddin, M. El Beheiry, J. Andilla, D. Ciepielewski, X. Darzacq, and M. Dahan, "PSF shaping using adaptive optics for three-dimensional single-molecule super-resolution imaging and tracking," Opt. Express 20, 4957 (2012); N. Piro, T. Pengo, N. Olivier, and S. Manley, "Improved 3D Superresolution Localization Microscopy Using Adaptive Optics," arXiv:1401.0879 [physics] (2014)). The cylindrical lens compound allows for optimization of the depth-dependent astigmatic effect by varying the distance between the two cylindrical components. Therefore, one can achieve an axial localization accuracy down to a few nanometers when tracking beads to stabilize the microscope at any imaging depth that the depth of field allows. For instance, FIGS. 4D and 4E show an optimized astigmatism effect used to track fluorescent beads when imaging at a depth of 8 µm (d=10 mm). To achieve a good sensitivity, d was adjusted such that moving the beads along the Z direction from +200 nm to −200 nm changes their ellipticity on the CCD from 1.5 to 0.75.

Generally, $\delta z$ is inversely proportional to the effective focal length of the ETL, $f_{ETL,eff}$, and is given by F. O. Fahrbach, F. F. Voigt, B. Schmid, F. Helmchen, and J. Huisken, "Rapid 3D light-sheet microscopy with a tunable lens," Opt. Express 21, 21010 (2013), where n is the refractive index of the immersion medium, $f_{RL2}$ is the focal length of relay lens 536 and M is the magnification on the CCD. $f_{ETL,eff}$ can be expressed as $f_{ETL,eff}^{-1} = f_{ETL}^{-1} + f_{CL2}^{-1} - df_{ETL}^{-1}f_{CL2}^{-1} \approx f_{ETL}^{-1} + f_{CL2}^{-1}$. Cylindrical lens 334 can be considered as an anamorphic Fourier transform system (I. Moreno, C. Ferreira, and M. M. Sánchez-López, "Ray matrix analysis of anamorphic fractional Fourier systems," J. Opt. A: Pure Appl. Opt. 8, 427 (2006); T. Szoplik, W. Kosek, and C. Ferreira, "Nonsymmetric Fourier transforming with an anamorphic system," Appl. Opt. 23, 905 (1984)) with a ray matrix in the X direction ($S_{CL2,x}$) given by:

$$S_{CL2,x} = \begin{pmatrix} 1 & 0 \\ f_{cl}^{-1} & 1 \end{pmatrix} \begin{pmatrix} 1 & d \\ 0 & 1 \end{pmatrix} \begin{pmatrix} 1 & 0 \\ -f_{cl}^{-1} & 1 \end{pmatrix} \qquad (1)$$

$$= \begin{pmatrix} 1 - df_{cl}^{-1} & 1 \\ -df_{cl}^{-2} & 1 + df_{cl}^{-1} \end{pmatrix},$$

which gives $f_{CL2} = -df_{cl}^{-2}$. In principle, the ray matrix for an individual cylindrical lens depends on a rotation matrix given by $$R(\alpha) = \begin{pmatrix} \cos(\alpha) & \sin(\alpha) \\ -\sin(\alpha) & \cos(\alpha) \end{pmatrix},$$

where α is the angle between the direction of the lens curvature and x-axis (in case of cylindrical lens 334, α=0 so R(α)=I).

δz for the current system was calculated as 12.6 μm, which is very close to the experimental measurement (<10% difference). The actual focal shift of ~11 μm was sufficient for imaging the transferrin receptors within B cells; the largest B cell which was observed had a thickness of ~10 μm. In addition, imaging at a depth larger than that greatly suffers from the sample-induced aberration and light scattering, which degrades the quality of the PSFs of single molecules. Note that δz can be easily extended by four times if one decreases M by two times (i.e. M=75).

In order to examine the performance of the stabilization system, the positional stability of 100 nm TetraSpeck™ beads was measured on EMCCD 328 for 10 min. Cameras were synchronized to obtain simultaneous exposure and readout on them. CCD 338 was set to acquire images at a rate of ~3 frames per second (exposure time=300 ms, piezo stage settling time=20 ms). Five Infrared fiducial marker located close to the center of the frame were tracked on CCD 338 to provide drift correction feedback. TetraSpeck beads were simultaneously imaged on EMCCD 328. A region of interest (ROI=10 pixel ×10 pixel) was set around each individual bead and ROIs were subsequently fitted using an error function to determine the lateral position of the beads as follows $$I_k(x, y) = I_0 \left( \text{erf}\left(\frac{x - x_0 + 0.5}{\sqrt{2}\,\sigma_x}\right) - \text{erf}\left(\frac{x - x_0 - 0.5}{\sqrt{2}\,\sigma_x}\right) \right) \times \left( \text{erf}\left(\frac{y - y_0 + 0.5}{\sqrt{2}\,\sigma_y}\right) - \text{erf}\left(\frac{y - y_0 - 0.5}{\sqrt{2}\,\sigma_y}\right) \right) + b_0, \quad (2)$$

where $I_k(x, y)$ is the expected number of photons for a given pixel k, $I_0$ is the total number of photons and $x_0$ and $y_0$ are the emitter positions in lateral directions. $\sigma_x$ and $\sigma_y$ are the standard deviations of the error function in X and Y, respectively, and $b_0$ is the background noise. The ellipticity, $R_{xy} = \sigma_x / \sigma_y$, was then calculated to determine the axial position of a bead according to the calibration curve shown in FIG. 4E. Displacement of beads was subsequently determined by comparing their shifted and initial positions. The mean of the displacements was then calculated and an appropriate voltage was applied to the piezo stage through a feedback loop.

FIG. 5A shows the positional stability of 100 nm TetraSpeck™ beads on EMCCD 528 with respect to time. Without the drift-correcting feedback mechanism loop enabled, the system drifts ~100 nm in the lateral direction and ~150 nm in the axial direction as measured over 10 min. With the feedback loop, however, the sample was stabilized in real-time and in three dimensions down to a few nanometers. FIG. 5B shows the root-mean-square (rms) of the beads' position, which was measured to be ~0.7 nm in the X 500C and Y 501C directions and ~2.7 nm in the Z 502C direction. The error in bead localization arises from the asymmetric emission profile of fluorescent beads, non-linearity in the photoelectric response of the camera and the associated computational errors. Note that the error in Z is about four times larger than that in X and Y. This is due to error propagation, which occurs by estimating the axial position of a bead using the widths of its PSF in X and Y directions, i.e. $W_x$ and $W_y$.

Super-resolution Imaging of Transferrin Receptors in B Cells

To demonstrate the application of the real-time 3D stabilization system, transferrin receptors in B cells were imaged at a depth of 8 μm. The transferrin receptor (TfR) is a membrane glycoprotein and mediates cellular uptake of iron from a plasma glycoprotein, transferrin. Iron uptake from transferrin involves the binding of transferrin to the TfR, internalization of transferrin within an endocytic vesicle by receptor-mediated endocytosis and the subsequent release of iron from the protein induced by a decrease in endosomal pH (P. Ponka and C. N. Lok, "The transferrin receptor: role in health and disease," The International Journal of Biochemistry & Cell Biology 31, 1111-1137 (1999)). In cell biology, TfR is a prototype marker for the recycling pathways and to probe both cell surface and endosomal structures in cells (H. Kobayashi and M. Fukuda, "Arf6, Rab11 and transferrin receptor define distinct populations of recycling endosomes," Commun. Integr. Biol. 6, e25036 (2013); R. S. Ajioka and J. Kaplan, "Intracellular pools of transferrin receptors result from constitutive internalization of unoccupied receptors," Proc. Natl. Acad. Sci. U.S.A. 83, 6445-6449 (1986); E. M. v. Dam, T. t. Broeke, K. Jansen, P. Spijkers, and W. Stoorvogel, "Endocytosed Transferrin Receptors Recycle via Distinct Dynamin and Phosphatidylinositol 3-Kinase-dependent Pathways," J. Biol. Chem. 277, 48876-48883 (2002)). This makes TfR an ideal choice for demonstrating the application of the stabilization system in deep super-resolution imaging.

The 639 nm laser was used at a relatively low intensity (<2 W/cm² at the sample) for illumination. A region of interest deep within the cell was located and the actual imaging depth was measured using the piezo stage controller. Before turning on the feedback mechanism loop, an appropriate current was applied to the ETL through the lens drive to obtain a clear image of the fiducial markers on the CCD. The current was adjusted such that the beads' ellipticity was in the range of 0.75-1.5. Up to five fiducial markers were typically tracked during image acquisition at a rate of 3 frames per second (fps).

Exposure time and gain of the CCD were gradually increased to compensate for the continuously decreasing number of photons emitted by infrared fluorescent beads. This ensures consistent accuracy in 3D localization of fiducial markers during the course of image acquisition. The intensity of the 639 nm laser was then increased to ~5 kW/cm² and the sample was photobleached for ~30 s. 40,000 frames were typically acquired on the EMCCD, at a rate of ~50 fps, to accumulate a sufficient number of single-molecule localizations. To reactivate dye molecules and compensate for a decreasing number of blinks due to photobleaching, the intensity of the 405 nm laser was increased in a stepwise fashion (from 0 to ~1 W/cm²) during image acquisition. The post-acquisition processing of images to determine the positions of single-molecules was performed using software written in MATLAB, as described in R. Tafteh, D. R. L. Scriven, E. D. W. Moore, and K. C. Chou, "Single molecule localization deep within thick cells; a novel super-resolution microscope," J. Biophoton 9, 155-160 (2016).

A drift-free super-resolution image of transferrin receptors in a B cell is shown in FIG. 6A. This image was constructed by plotting the density map of single-molecule localizations (nearest neighborhood distance (NND)=100 nm). The corresponding image with drift is shown in FIG. 6B. This was obtained by computationally adding the actual drift in all directions that occurred during image acquisition to the drift-free image, as shown in FIG. 6C. Insets of the regions as marked in FIGS. 6A and 6B are shown in FIGS. 6D and 6E, respectively. The drift-free super-resolution image shown in FIG. 6D reveals that transferrin receptors exist as well-defined clusters, which are punctate with a significantly higher density compared to the corresponding clusters in the drifted image shown in FIG. 6E. Specifically, clusters in the drifted image are elongated and blurred. The three-dimensional representations of regions marked in Figured 6D and 6E in are shown in FIGS. 6F and 6G, respectively. The clusters in the drift-free super-resolution image shown in FIG. 6F are isotropic and distinct from cluster to cluster. However, the corresponding clusters in the drifted image shown in FIG. 6G are non-isotropic and difficult to discern as they are fused together.

To quantitatively analyze the effects of drift on topology and density of TfR clusters, a novel clustering method based on Voronoïtessellation was used (F. Levet, E. Hosy, A. Kechkar, C. Butler, A. Beghin, D. Choquet, and J.-B. Sibarita, "SR-Tesseler: a method to segment and quantify localization-based super-resolution microscopy data," Nat. Methods 12, 1065-1071 (2015); D. Baddeley, "Detecting nano-scale protein clustering," Nat. Methods 12, 1019-1020 (2015)). Voronoïtessellation is based on the principle of subdividing an image into polygonal regions centered on seeds. Any point within a polygon is closer to its associated seed than it is to any other seed. FIGS. 6H and 6I show tessellation maps of the regions as marked in Figured 6D and 6E respectively; segmented clusters are shaded. Segmentation of the localization data points into clusters was performed using a single parameter, i.e. density threshold, which was set to twice the average localization density. Comparing the regions marked by dashed lines in FIGS. 6H and 6I, one can see that drift not only affects the separation of the closely spaced transferrin clusters as between regions 610A and 611A, and between regions 610B and 611B, but it also affects the topology of the clusters (compare the clusters in region 610C with 611C).

A more comprehensive analysis of transferrin clusters in FIGS. 6J and 6K reveals that drift has significant influences on the distribution of cluster density (i.e. number of localization per cluster per unit area, and cluster size). Overall, the TfR clusters in the drift-free image are smaller than those in the drifted image and show higher cluster density. This is attributed to the sample drift, which extends the area of clusters and leads to a lowered cluster density. TfR exist as heterogeneous nanoclusters in B cells (as shown by bimodal size distribution in FIG. 6K). This data is consistent with electron microscopy (EM) studies, which show that size of TfR containing vesicles varies from 30 nm to 160 nm (R. S. Ajioka and J. Kaplan, "Intracellular pools of transferrin receptors result from constitutive internalization of unoccupied receptors," Proc. Natl. Acad. Sci. U.S.A. 83, 6445-6449 (1986); C. Harding, J. Heuser, and P. Stahl, "Receptor-mediated endocytosis of transferrin and recycling of the transferrin receptor in rat reticulocytes," The Journal of Cell Biology 97, 329-339 (1983); C. R. Hopkins, "Intracellular routing of transferrin and transferrin receptors in epidermoid carcinoma A431 cells," Cell 35, 321-330 (1983); B. T. Pan, K. Teng, C. Wu, M. Adam, and R. M. Johnstone, "Electron microscopic evidence for externalization of the transferrin receptor in vesicular form in sheep reticulocytes," The Journal of Cell Biology 101, 942-948 (1985)).

Figure 6L:
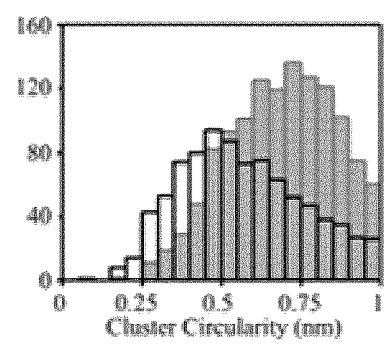

FIG. 6L shows distribution of the cluster circularity shows that transferrin clusters in the drift-free super-resolution image are more circular compared to those in the drifted image. Cluster circularity was calculated as the ratio of the major and minor axes of a cluster. The majority of TfR clusters in the drifted image have a circularity of 0.5, compared to 0.75 in the drift-free image.

Interpretation of Terms

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms;

"optical radiation" refers to electromagnetic radiation in the wavelength range of 100 nm to 1 mm;

"deep imaging" is imaging at least 1 μm deep in a sample.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Such hardware may be configured for example to provide closed-loop control of a stage and/or image processing as described herein. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Software and other modules may reside on servers, workstations, personal computers, microscope controllers, and other devices suitable for the purposes described herein. Those skilled in the relevant art will appreciate that aspects of the system can be practised with other communications, data processing, or computer system configurations.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

The following references relate generally to the field of the disclosure and include information that provides background for better understanding of the invention:

1. Pertsinidis, A., Zhang, Y. & Chu, S. *Nature* 466, 647-651 (2010).
2. Carter, A. R. et al. *Appl. Opt.* 46, 421-427 (2007).
3. Mennella, V. et al. *Nat. Cell Biol.* 14, 1159-1168 (2012).
4. Geisler, C. et al. *Opt. Express* 20 (2012).
5. Huang, B., Jones, S. A., Brandenburg, B. & Zhuang, X. *Nat. Meth.* 5, 1047-1052 (2008).
6. Huang, B., Wang, W., Bates, M. & Zhuang, X. *Science* 319, 810-813 (2008).
7. McGorty, R., Schnitzbauer, J., Zhang, W. & Huang, B. *Opt. Lett.* 39, 275-278 (2014).
8. Henriques, R. et al. *Nat. Meth.* 7, 339-340 (2010).
9. Wolter, S. et al. *Nat. Meth.* 9, 1040-1041 (2012).
10. Jones, S. A., Shim, S.-H., He, J. & Zhuang, X. *Nat. Meth.* 8, 499-505 (2011).
11. Chen-Izu, Y. et al. *Biophys. J.* 91, 1-13 (2006).
12. Babcock, H., Sigal, Y. M. & Zhuang, X. *Opt. Nanoscopy* 1 (2012).
13. Cox, S. et al. *Nat. Meth.* 9, 195-200 (2012).
14. Holden, S. J., Uphoff, S. & Kapanidis, A. N. *Nat. Meth.* 8, 279-280 (2011).
15. Radermacher, M. et al. *J. Cell Biol.* 127, 411-423 (1994).
16. Asghari, P. et al. *Circ. Res.* 115, 252-262 (2014).
17. Huang, F., Schwartz, S. L., Byars, J. M. & Lidke, K. A. *Biomedical Optics Express* 2, 1377-1393 (2011)
18. Pertsinidis, A., Zhang, Y. & Chu, S. Subnanometre single-molecule localization, registration and distance measurements. *Nature* 466, 647-651 (2010)
19. Chen-Izu, Y. et al. *Biophysical Journal* 91, 1-13 (2006)
20. Rodrigues, B. a. S., D. L. *Preparation of cardiomyocytes.* (CRC Press, 1997)
21. Volkmann, H., "Ernst Abbe and His Work," *Appl. Opt.* 5, 1720 (1966).
22. Rayleigh, L., "XV. On the theory of optical images, with special reference to the microscope," *Philosophical Magazine Series* 5 42, 167-195 (1896).
23. Cremer, C. and Masters, B. R., "Resolution enhancement techniques in microscopy," *EPJ H* 38, 281-344 (2013).
24. McCutchen, C. W., "Superresolution in Microscopy and the Abbe Resolution Limit," *J. Opt. Soc. Am.* 57, 1190 (1967).
25. Yildiz, A., Forkey, J. N., McKinney, S. A., Ha, T., Goldman, Y. E., and Selvin, P. R., "Myosin V walks hand-over-hand: single fluorophore imaging with 1.5-nm localization," *Science* (New York, N.Y.) 300, 2061-2065 (2003).
26. Yildiz, A., Tomishige, M., Vale, R. D., and Selvin, P. R., "Kinesin walks hand-over-hand," *Science* (New York, N.Y.) 303, 676-678 (2004).
27. Betzig, E., Patterson, G. H., Sougrat, R., Lindwasser, O. W., Olenych, S., Bonifacino, J. S., Davidson, M. W., Lippincott-Schwartz, J., and Hess, H. F., "Imaging Intracellular Fluorescent Proteins at Nanometer Resolution," *Science* 313, 1642-1645 (2006).
28. Rust, M. J., Bates, M., and Zhuang, X., "Sub-diffraction-limit imaging by stochastic optical reconstruction microscopy (STORM)," *Nat. Methods* 3, 793-796 (2006).
29. G. Giannone, E. Hosy, F. Levet, A. Constals, K. Schulze, A. I. Sobolevsky, M. P. Rosconi, E. Gouaux, R. Tampe, D. Choquet, and L. Cognet, "Dynamic superresolution imaging of endogenous proteins on living cells at ultra-high density," *Biophys. J.* 99, 1303-1310 (2010).
30. R. J. Ober, S. Ram, and E. S. Ward, "Localization Accuracy in Single-Molecule Microscopy," *Biophys. J.* 86, 1185-1200 (2004).
31. S. H. Lee, M. Baday, M. Tjioe, P. D. Simonson, R. Zhang, E. Cai, and P. R. Selvin, "Using fixed fiducial markers for stage drift correction," *Opt. Express* 20, 12177-12183 (2012).

32. A. Pertsinidis, Y. Zhang, and S. Chu, "Subnanometre single-molecule localization, registration and distance measurements," *Nature* 466, 647-651 (2010).
33. A. R. Carter, G. M. King, T. A. Ulrich, W. Halsey, D. Alchenberger, and T. T. Perkins, "Stabilization of an optical microscope to 0.1 nm in three dimensions," *Appl. Opt.* 46, 421-427 (2007).
34. R. McGorty, D. Kamiyama, and B. Huang, "Active microscope stabilization in three dimensions using image correlation," in *Opt. Nanoscopy*, (2013).
35. V. Mennella, B. Keszthelyi, K. L. McDonald, B. Chhun, F. Kan, G. C. Rogers, B. Huang, and D. A. Agard, "Subdiffraction-resolution fluorescence microscopy reveals a domain of the centrosome critical for pericentriolar material organization," *Nat. Cell Biol.* 14, 1159-1168 (2012).
36. C. Geisler, T. Hotz, A. Schönle, S. W. Hell, A. Munk, and A. Egner, "Drift estimation for single marker switching based imaging schemes," *Opt. Express* 20 (2012).
37. M. J. Mlodzianoski, J. M. Schreiner, S. P. Callahan, K. Smolková, A. Dlasková, J. Santorová, P. Ježek, and J. Bewersdorf, "Sample drift correction in 3D fluorescence photoactivation localization microscopy," *Opt. Express* 19, 15009-15019 (2011).
38. G. Beadie, M. L. Sandrock, M. J. Wiggins, R. S. Lepkowicz, J. S. Shirk, M. Ponting, Y. Yang, T. Kazmierczak, A. Hiltner, and E. Baer, "Tunable polymer lens," *Opt. Express* 16, 11847-11857 (2008).
39. H. Ren, H. Xianyu, S. Xu, and S.-T. Wu, "Adaptive dielectric liquid lens," *Opt. Express* 16, 14954 (2008).
40. O. Pishnyak, S. Sato, and O. D. Lavrentovich, "Electrically tunable lens based on a dual-frequency nematic liquid crystal," *Appl. Opt.* 45, 4576 (2006).
41. S. Kuiper, B. H. Hendriks, L. J. Huijbregts, A. M. Hirschberg, C. A. Renders, and M. A. van As, "Variable-focus liquid lens for portable applications," in 2004, 100-109.
42. R. Tafteh, D. R. L. Scriven, E. D. W. Moore, and K. C. Chou, "Single molecule localization deep within thick cells; a novel super-resolution microscope," *J. Biophoton* 9, 155-160 (2016).
43. B. Huang, W. Wang, M. Bates, and X. Zhuang, "Three-Dimensional Super-Resolution Imaging by Stochastic Optical Reconstruction Microscopy," *Science* 319, 810-813 (2008).
44. S. A. Freeman, V. Jaumouillé, K. Choi, B. E. Hsu, H. S. Wong, L. Abraham, M. L. Graves, D. Coombs, C. D. Roskelley, R. Das, S. Grinstein, and M. R. Gold, "Toll-like receptor ligands sensitize B-cell receptor signalling by reducing actin-dependent spatial confinement of the receptor," *Nat Commun* 6, 6168 (2015).
45. J. Futran, J. D. Kemp, E. H. Field, A. Vora, and R. F. Ashman, "Transferrin receptor synthesis is an early event in B cell activation," *Journal of Immunology* (Baltimore, Md.: 1950) 143, 787-792 (1989).
46. L. M. Neckers, G. Yenokida, and S. P. James, "The role of the transferrin receptor in human B lymphocyte activation," *Journal of Immunology* (Baltimore, Md.: 1950) 133, 2437-2441 (1984).
47. G. Eberle, V. Chiron, and K. Wegener, "Simulation and Realization of a Focus Shifting Unit using a Tunable Lens for 3D Laser Material Processing," *Physics Procedia* 41, 441-447 (2013).
48. I. Izeddin, M. El Beheiry, J. Andilla, D. Ciepielewski, X. Darzacq, and M. Dahan, "PSF shaping using adaptive optics for three-dimensional single-molecule super-resolution imaging and tracking," *Opt. Express* 20, 4957 (2012).
49. N. Piro, T. Pengo, N. Olivier, and S. Manley, "Improved 3D Superresolution Localization Microscopy Using Adaptive Optics," arXiv:1401.0879 [physics] (2014).
50. F. O. Fahrbach, F. F. Voigt, B. Schmid, F. Helmchen, and J. Huisken, "Rapid 3D light-sheet microscopy with a tunable lens," *Opt. Express* 21, 21010 (2013).
51. I. Moreno, C. Ferreira, and M. M. Sánchez-López, "Ray matrix analysis of anamorphic fractional Fourier systems," *J. Opt. A: Pure Appl. Opt.* 8, 427 (2006).
52. T. Szoplik, W. Kosek, and C. Ferreira, "Nonsymmetric Fourier transforming with an anamorphic system," *Appl. Opt.* 23, 905 (1984).
53. P. Ponka and C. N. Lok, "The transferrin receptor: role in health and disease," The *International Journal of Biochemistry & Cell Biology* 31, 1111-1137 (1999).
54. H. Kobayashi and M. Fukuda, "Arf6, Rab11 and transferrin receptor define distinct populations of recycling endosomes," *Commun. Integr. Biol.* 6, e25036 (2013).
55. R. S. Ajioka and J. Kaplan, "Intracellular pools of transferrin receptors result from constitutive internalization of unoccupied receptors," *Proc. Natl. Acad. Sci. U.S.A.* 83, 6445-6449 (1986).
56. E. M. v. Dam, T. t. Broeke, K. Jansen, P. Spijkers, and W. Stoorvogel, "Endocytosed Transferrin Receptors Recycle via Distinct Dynamin and Phosphatidylinositol 3-Kinase-dependent Pathways," *J. Biol. Chem.* 277, 48876-48883 (2002).
57. F. Levet, E. Hosy, A. Kechkar, C. Butler, A. Beghin, D. Choquet, and J.-B. Sibarita, "SR-Tesseler: a method to segment and quantify localization-based super-resolution microscopy data," *Nat. Methods* 12, 1065-1071 (2015).
58. D. Baddeley, "Detecting nano-scale protein clustering," *Nat. Methods* 12, 1019-1020 (2015).
59. C. Harding, J. Heuser, and P. Stahl, "Receptor-mediated endocytosis of transferrin and recycling of the transferrin receptor in rat reticulocytes," *The Journal of Cell Biology* 97, 329-339 (1983).
60. C. R. Hopkins, "Intracellular routing of transferrin and transferrin receptors in epidermoid carcinoma A431 cells," Cell 35, 321-330 (1983).
61. B. T. Pan, K. Teng, C. Wu, M. Adam, and R. M. Johnstone, "Electron microscopic evidence for externalization of the transferrin receptor in vesicular form in sheep reticulocytes," *The Journal of Cell Biology* 101, 942-948 (1985).

What is claimed is:

1. A method for imaging a sample, the method comprising:
  providing one or more fiducial markers near the sample;
  imaging the sample using a first imaging system comprising an objective lens; and
  while imaging the sample:
    imaging the one or more fiducial markers with a second imaging system by way of the objective lens and focusing the second imaging system independently of the first imaging system;
    processing images of the one or more fiducial markers obtained by the second imaging system to yield a measure of drift of the fiducial markers relative to the objective lens; and
    controlling an actuator to correct for the drift.

2. A method according to claim 1 wherein imaging the sample comprises illuminating the sample with light of a first wavelength and detecting light of one or more second wavelengths different from the first wavelength.

3. A method according to claim 2, comprising directing the light of the first wavelength for oblique incidence on the sample.

4. A method according to claim 2, wherein imaging the fiducial markers comprises illuminating the fiducial markers with light of a fourth wavelength different from the first and second wavelengths and detecting light of a third wavelength.

5. A method according to claim 4, wherein illuminating the one or more fiducial markers with light of the fourth wavelength comprises passing light from a second laser source through the objective lens and wherein illuminating the sample with light of the first wavelength comprises passing light from a first laser source through the objective lens.

6. A method according to claim 1, comprising providing an asymmetrical optical element in an imaging path of the second imaging system wherein processing images of the one or more fiducial markers comprises determining a distortion in the images of the fiducial markers due to astigmatism and determining a component of the drift in a direction along a z-axis parallel to an optical axis of the objective lens based on the distortion.

7. A method according to claim 6, wherein determining the distortion comprises determining an aspect ratio of height to width in images of the fiducial markers and if the aspect ratio is less than a reference value operating the actuator to move the sample in one direction along the z-axis and if the aspect ratio is greater than the reference amount operating the actuator to move the sample in a second direction opposite to the first direction along the z-axis.

8. A method according to claim 1, wherein the actuator comprises a stage operative to independently control a position of the sample relative to the objective lens in two dimensions orthogonal to an optical axis of the objective lens.

9. A method according to claim 1, wherein the second imaging system is selective for light having first wavelength characteristics and the first imaging system is insensitive to light having the first wavelength characteristics.

10. A method according to claim 1, wherein imaging the sample comprises focusing the first imaging system on a sample plane of the sample, and imaging the fiducial markers comprises focusing the second imaging system on a fiducial marker plane of the one or more fiducial markers wherein the sample plane is spaced apart from the marker plane by at least 500 nm.

11. A method according to claim 10 wherein the sample plane is deeper than the fiducial marker plane.

12. A method according to claim 10, wherein the fiducial marker plane coincides with a surface of a coverslip.

13. A method according to claim 1, comprising automatically focusing the second imaging system on the one or more fiducial markers.

14. A method according to claim 1, wherein the one or more fiducial markers comprise a plurality of fiducial markers and processing images of the one or more fiducial markers obtained by the second imaging system to yield a measure of drift comprises separately determining a drift of each of the plurality of fiducial markers and averaging the drifts.

15. A method according to claim 1, wherein imaging the sample comprises collecting light over a period of at least 2 minutes and imaging the fiducial markers using an exposure time of less than 500 ms.

16. A method according to claim 1, comprising providing an electrically tunable lens between the objective lens and the second imaging system and, while imaging the sample with the first imaging system, adjusting the tunable lens to focus the second imaging system on the fiducial markers.

17. A method according to claim 1, comprising while imaging the sample, gradually increasing an exposure time of the second imaging system.

18. A method according to claim 1, comprising while imaging the sample, gradually increasing a gain of the second imaging system.

19. A method according to claim 1, wherein imaging the fiducial markers comprises illuminating the fiducial markers with light from a light source, and while imaging the sample, increasing an intensity of the light source.

20. A method according to claim 1, wherein the first and second imaging systems are the same system, and imaging the sample comprises alternating the focus of the imaging system between the fiducial markers and the sample.

21. A method for stabilizing an image generated by an optical microscope, the method comprising:
illuminating a sample and a fiducial element held on a nanopositioning stage, the sample comprising a target element having a positional drift;
detecting photons from the fiducial element and the target element by independently focusing the photons from the fiducial element and the target element onto independent first and second image sensors, wherein the photons emitted by the target element and the fiducial element are respectively detected by the independent first and second image sensors allowing stabilization when the target element and the fiducial element are located at a different depths;
providing an adjustable relay lens in an optical path of one of the first and second image sensors and controlling the relay lens to focus the first and second image sensors at different focal planes;
correcting the positional drift of the sample by processing an output of the second image sensor using an algorithm configured to calculate changes in location of the fiducial element; and
performing closed-loop feedback control of the nanopositioning stage using the calculated changes in location of the fiducial element, thereby stabilizing an image of the sample.

22. A method according to claim 21, wherein the image of the sample is a two-dimensional or three-dimensional image and the method comprises stabilizing the image in three dimensions.

23. A method according to claim 21, wherein the nanopositioning stage is a three-axis nanopositioning stage.

24. A method according to claim 21, wherein the fiducial element is affixed to a coverslip and the sample is imaged through the coverslip.

25. A method according to claim 21, wherein the target element and the fiducial element are spaced apart along a z direction aligned with an optical axis of the optical microscope.

26. A method of stabilizing an image generated by an optical microscope comprising:
applying a light source to a sample and a fiducial element held on a nanopositioning stage, the sample comprising a target element and having a positional drift;

detecting photons emitted from the fiducial element with a first image sensor;

detecting photons emitted from the target element with a second image sensor; and correcting the positional drift of the sample using an algorithm configured to calculate a location of the fiducial element and having closed-loop feedback control of the nanopositioning stage, thereby stabilizing the image;

wherein a relay lens is used in an optical path of either the first image sensor or the second image sensor to enable the first image sensor and the second image sensor to independently focus at different focal planes.

27. The method according to claim 26, wherein:
the image of the target element on the second image sensor is brought into focus; and
a relay lens is used to bring the image of the fiducial element into focus on the first image sensor;
wherein the images captured by both the first image sensor and the second image sensor are in focus.

28. A super-resolution microscopy system comprising:
an objective lens;
a stage;
a first imaging system operative to image a sample on the stage by way of the objective lens;
a second imaging system operative to image one or more fiducial markers on the stage by way of the objective lens;
one or more actuators connected to move the sample relative to the objective lens; and
a controller comprising a processor configured to process image data from the second imaging system to determine a drift of the one or more fiducial markers and to control the one or more actuators to compensate for the drift;
wherein the first and second imaging system are separately focusable.

29. A super resolution microscopy system according to claim 28 wherein the second imaging system comprises an imaging light sensor, a wavelength selector arranged to direct light having selected wavelength characteristics to the imaging light sensor and an adjustable focusing element between the wavelength selector and the imaging light sensor.

30. A super resolution microscopy system according to claim 29 comprising an asymmetrical optical element in an optical path of the imaging light sensor.

31. A super resolution microscopy system according to claim 30 wherein the asymmetrical optical element comprises a cylindrical lens.

32. A system for stabilizing an image generated by an optical microscope, the system comprising:
a light source configured to provide light to a sample and a fiducial element held on a nanopositioning stage, the sample comprising a target element and having a positional drift;
an optical system configured to independently focus photons emitted by the fiducial element onto a first image sensor and photons emitted by the target element onto a second image sensor, the optical system comprising an adjustable relay lens in an optical path of one of the first and second image sensors, the relay lens controllable to focus the first and second image sensors at different focal planes;
the first image sensor, configured to detect photons emitted by the fiducial element;
the second image sensor, configured to detect photons emitted by the target element; and
a computer comprising an algorithm configured to calculate the location of the fiducial element and having closed-loop feedback control of the nanopositioning stage, thereby stabilizing the image generated by the optical microscope.

33. A system for stabilizing an image generated by an optical microscope, the system comprising:
a first light source configured to provide light to a sample, the sample comprising a target element and having a positional drift;
a second light source configured to provide light to a fiducial element held on a nanopositioning stage wherein the first light source and the second light source emit light at different wavelengths;
a dichroic mirror arranged to separate the light from the first light source and the second light source;
a first image sensor, configured to detect photons emitted by the fiducial element;
a second image sensor, configured to detect photons emitted by the target element;
a first relay lens positioned between the dichroic mirror and the first image sensor, such that the relay lens can adjust a focal plane of the first image sensor independently from a focal plane of the second image sensor; and
a computer comprising an algorithm configured to calculate a location of the fiducial element and having closed-loop feedback control of the nanopositioning stage, thereby stabilizing the image generated by the optical microscope.

34. The system according to claim 33, comprising a second relay lens positioned between the dichroic mirror and the second image sensor, such that the second relay lens can adjust the focal plane of the second image sensor independently from that of the first image sensor.

35. A system for stabilizing an image generated by an optical microscope, the system comprising:
a first light source configured to provide light to a sample, the sample comprising a target element and having a positional drift;
a second light source configured to provide light to a fiducial element held on a nanopositioning stage wherein the first light source and the second light source emit light at different wavelengths;
a dichroic mirror arranged to separate the light from the first light source and the second light source;
a first image sensor, configured to detect photons emitted by the fiducial element;
a second image sensor, configured to detect photons emitted by the target element;
a relay lens positioned between the dichroic mirror and the second image sensor, such that the relay lens can adjust the focal plane of the second image sensor independently from that of the first image sensor; and
a computer comprising an algorithm configured to calculate a location of the fiducial element and having closed-loop feedback control of the nanopositioning stage, thereby stabilizing the image generated by the optical microscope.

* * * * *